(12) United States Patent
Raridan et al.

(10) Patent No.: US 7,657,296 B2
(45) Date of Patent: Feb. 2, 2010

(54) UNITARY MEDICAL SENSOR ASSEMBLY AND TECHNIQUE FOR USING THE SAME

(75) Inventors: William Raridan, Pleasanton, CA (US); George L. Matlock, Pleasanton, CA (US); Joseph Coakley, Dublin, CA (US); Darius Eghbal, Oakland, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 525 days.

(21) Appl. No.: 11/495,392

(22) Filed: Jul. 28, 2006

(65) Prior Publication Data

US 2007/0032712 A1 Feb. 8, 2007

Related U.S. Application Data

(63) Continuation of application No. 11/199,525, filed on Aug. 8, 2005.

(51) Int. Cl.
*A61B 5/145* (2006.01)
(52) U.S. Cl. ...................................... 600/344
(58) Field of Classification Search ................ 600/323, 600/344
See application file for complete search history.

(56) References Cited

U.S. PATENT DOCUMENTS

| | | | |
|---|---|---|---|
| 3,403,555 A | 10/1968 | Versaci et al. | |
| 3,536,545 A | 10/1970 | Traynor et al. | |
| D222,454 S | 10/1971 | Beeber | |
| 3,721,813 A | 3/1973 | Condon et al. | |
| D250,275 S | 11/1978 | Bond | |
| D251,387 S | 3/1979 | Ramsay et al. | |
| D262,488 S | 12/1981 | Rossman et al. | |
| 4,334,544 A | 6/1982 | Hill et al. | |

(Continued)

FOREIGN PATENT DOCUMENTS

CN 11080192 11/2007

(Continued)

OTHER PUBLICATIONS

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).

(Continued)

*Primary Examiner*—Eric F Winakur
*Assistant Examiner*—Etsub D Berhanu
(74) *Attorney, Agent, or Firm*—Fletcher Yoder

(57) ABSTRACT

A sensor assembly is provided that includes a frame having a first portion and a second portion connected by a hinge. An emitter and a detector are disposed on the frame. A coating is provided over the frame, the emitter and the detector to form a unitary sensor assembly. The sensor assembly also includes a resistance-providing component disposed generally about the hinge. In one embodiment, the sensor assembly may be placed on a patient's finger, toe, ear, and so forth to obtain pulse oximetry or other physiological measurements. A method of manufacturing the sensor assembly is also provided as is a method of cleaning a fluid-tight sensor assembly.

28 Claims, 5 Drawing Sheets

U.S. PATENT DOCUMENTS

| | | |
|---|---|---|
| 4,350,165 A | 9/1982 | Striese |
| 4,353,372 A | 10/1982 | Ayer |
| 4,380,240 A | 4/1983 | Jöbsis et al. |
| 4,406,289 A | 9/1983 | Wesseling et al. |
| 4,510,551 A | 4/1985 | Brainard, II |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,722,120 A | 2/1988 | Lu |
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Büttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hausman et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Freidman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |

| | | | | | |
|---|---|---|---|---|---|
| 5,309,908 A | 5/1994 | Freidman et al. | 5,529,064 A | 6/1996 | Rall et al. |
| 5,311,865 A | 5/1994 | Mayeux | 5,533,507 A | 7/1996 | Potratz et al. |
| 5,313,940 A | 5/1994 | Fuse et al. | 5,551,423 A | 9/1996 | Sugiura |
| 5,323,776 A | 6/1994 | Blakeley et al. | 5,551,424 A | 9/1996 | Morrison et al. |
| 5,329,922 A | 7/1994 | Atlee, III | 5,553,614 A | 9/1996 | Chance |
| 5,337,744 A | 8/1994 | Branigan | 5,553,615 A | 9/1996 | Carim et al. |
| 5,339,810 A | 8/1994 | Ivers et al. | 5,555,882 A | 9/1996 | Richardson et al. |
| 5,343,818 A | 9/1994 | McCarthy et al. | 5,558,096 A | 9/1996 | Palatnik |
| 5,343,869 A | 9/1994 | Pross et al. | 5,560,355 A | 10/1996 | Merchant et al. |
| 5,348,003 A | 9/1994 | Caro | 5,564,417 A | 10/1996 | Chance |
| 5,348,004 A | 9/1994 | Hollub et al. | 5,575,284 A | 11/1996 | Athan et al. |
| 5,349,519 A | 9/1994 | Kaestle | 5,575,285 A | 11/1996 | Takanashi et al. |
| 5,349,952 A | 9/1994 | McCarthy et al. | 5,577,500 A | 11/1996 | Potratz |
| 5,349,953 A | 9/1994 | McCarthy et al. | 5,582,169 A | 12/1996 | Oda et al. |
| 5,351,685 A | 10/1994 | Potratz | 5,584,296 A | 12/1996 | Cui et al. |
| 5,353,799 A | 10/1994 | Chance | 5,588,425 A | 12/1996 | Sackner et al. |
| 5,355,880 A | 10/1994 | Thomas et al. | 5,588,427 A | 12/1996 | Tien |
| 5,355,882 A | 10/1994 | Ukawa et al. | 5,590,652 A | 1/1997 | Inai |
| 5,361,758 A | 11/1994 | Hall et al. | 5,595,176 A | 1/1997 | Yamaura |
| 5,365,066 A | 11/1994 | Krueger, Jr. et al. | 5,596,986 A | 1/1997 | Goldfarb |
| 5,368,025 A | 11/1994 | Young et al. | 5,611,337 A | 3/1997 | Bukta |
| 5,368,026 A | 11/1994 | Swedlow et al. | 5,617,852 A | 4/1997 | MacGregor |
| 5,368,224 A | 11/1994 | Richardson et al. | 5,619,992 A | 4/1997 | Guthrie et al. |
| 5,372,136 A | 12/1994 | Steuer et al. | 5,626,140 A | 5/1997 | Feldman et al. |
| 5,377,675 A | 1/1995 | Ruskewicz et al. | 5,630,413 A | 5/1997 | Thomas et al. |
| 5,385,143 A | 1/1995 | Aoyagi | 5,632,272 A | 5/1997 | Diab et al. |
| 5,387,122 A | 2/1995 | Goldberger et al. | 5,632,273 A | 5/1997 | Suzuki |
| 5,390,670 A | 2/1995 | Centa et al. | 5,634,459 A | 6/1997 | Gardosi |
| 5,392,777 A | 2/1995 | Swedlow et al. | 5,638,593 A | 6/1997 | Gerhardt et al. |
| 5,398,680 A | 3/1995 | Polson et al. | 5,638,816 A | 6/1997 | Kiani-Azarbayjany et al. |
| 5,402,777 A | 4/1995 | Warring et al. | 5,638,818 A | 6/1997 | Diab et al. |
| 5,402,779 A | 4/1995 | Chen et al. | 5,645,060 A | 7/1997 | Yorkey et al. |
| 5,411,023 A | 5/1995 | Morris, Sr. et al. | 5,645,440 A | 7/1997 | Tobler et al. |
| 5,411,024 A | 5/1995 | Thomas et al. | 5,660,567 A | 8/1997 | Nierlich et al. |
| 5,413,099 A | 5/1995 | Schmidt et al. | 5,662,105 A | 9/1997 | Tien |
| 5,413,100 A | 5/1995 | Barthelemy et al. | 5,662,106 A | 9/1997 | Swedlow et al. |
| 5,413,101 A | 5/1995 | Sugiura | 5,664,270 A | 9/1997 | Bell et al. |
| 5,413,102 A | 5/1995 | Schmidt et al. | 5,666,952 A | 9/1997 | Fuse et al. |
| 5,417,207 A | 5/1995 | Young et al. | 5,671,529 A | 9/1997 | Nelson |
| 5,421,329 A | 6/1995 | Casciani et al. | 5,673,692 A | 10/1997 | Schulze et al. |
| 5,425,360 A | 6/1995 | Nelson | 5,673,693 A | 10/1997 | Solenberger |
| 5,425,362 A | 6/1995 | Siker et al. | 5,676,139 A | 10/1997 | Goldberger et al. |
| 5,427,093 A | 6/1995 | Ogawa et al. | 5,676,141 A | 10/1997 | Hollub |
| 5,429,128 A | 7/1995 | Cadell et al. | 5,678,544 A | 10/1997 | DeLonzor et al. |
| 5,429,129 A | 7/1995 | Lovejoy et al. | 5,680,857 A | 10/1997 | Pelikan et al. |
| 5,431,159 A | 7/1995 | Baker et al. | 5,685,299 A | 11/1997 | Diab et al. |
| 5,431,170 A | 7/1995 | Mathews | 5,685,301 A | 11/1997 | Klomhaus |
| 5,437,275 A | 8/1995 | Amundsen et al. | 5,687,719 A | 11/1997 | Sato et al. |
| 5,438,986 A | 8/1995 | Disch et al. | 5,687,722 A | 11/1997 | Tien et al. |
| 5,448,991 A | 9/1995 | Polson et al. | 5,692,503 A | 12/1997 | Kuenstner |
| 5,452,717 A | 9/1995 | Branigan et al. | 5,692,505 A | 12/1997 | Fouts |
| 5,465,714 A | 11/1995 | Scheuing | 5,709,205 A | 1/1998 | Bukta |
| 5,469,845 A | 11/1995 | DeLonzor et al. | 5,713,355 A | 2/1998 | Richardson et al. |
| RE35,122 E | 12/1995 | Corenman et al. | 5,724,967 A | 3/1998 | Venkatachalam |
| 5,482,034 A | 1/1996 | Lewis et al. | 5,727,547 A | 3/1998 | Levinson et al. |
| 5,482,036 A | 1/1996 | Diab et al. | 5,730,124 A | 3/1998 | Yamauchi |
| 5,485,847 A | 1/1996 | Baker, Jr. | 5,731,582 A | 3/1998 | West |
| 5,490,505 A | 2/1996 | Diab et al. | D393,830 S | 4/1998 | Tobler et al. |
| 5,490,523 A | 2/1996 | Isacson et al. | 5,743,260 A | 4/1998 | Chung et al. |
| 5,491,299 A | 2/1996 | Naylor et al. | 5,743,262 A | 4/1998 | Lepper, Jr. et al. |
| 5,494,032 A | 2/1996 | Robinson et al. | 5,743,263 A | 4/1998 | Baker, Jr. |
| 5,494,043 A | 2/1996 | O'Sullivan et al. | 5,746,206 A | 5/1998 | Mannheimer |
| 5,497,771 A | 3/1996 | Rosenheimer | 5,746,697 A | 5/1998 | Swedlow et al. |
| 5,499,627 A | 3/1996 | Steuer et al. | 5,752,914 A | 5/1998 | DeLonzor et al. |
| 5,503,148 A | 4/1996 | Pologe et al. | 5,755,226 A | 5/1998 | Carim et al. |
| 5,505,199 A | 4/1996 | Kim | 5,758,644 A | 6/1998 | Diab et al. |
| 5,507,286 A | 4/1996 | Solenberger | 5,760,910 A | 6/1998 | Lepper, Jr. et al. |
| 5,511,546 A | 4/1996 | Hon | 5,766,125 A | 6/1998 | Aoyagi et al. |
| 5,517,988 A | 5/1996 | Gerhard | 5,766,127 A | 6/1998 | Pologe et al. |
| 5,520,177 A | 5/1996 | Ogawa et al. | 5,769,785 A | 6/1998 | Diab et al. |
| 5,521,851 A | 5/1996 | Wei et al. | 5,772,587 A | 6/1998 | Gratton et al. |
| 5,522,388 A | 6/1996 | Ishikawa et al. | 5,774,213 A | 6/1998 | Trebino et al. |
| 5,524,617 A | 6/1996 | Mannheimer | 5,776,058 A | 7/1998 | Levinson et al. |

| | | | | | |
|---|---|---|---|---|---|
| 5,776,059 A | 7/1998 | Kaestle | 5,954,644 A | 9/1999 | Dettling et al. |
| 5,779,630 A | 7/1998 | Fein et al. | 5,957,840 A | 9/1999 | Terasawa et al. |
| 5,779,631 A | 7/1998 | Chance | 5,960,610 A | 10/1999 | Levinson et al. |
| 5,782,237 A | 7/1998 | Casciani et al. | 5,961,450 A | 10/1999 | Merchant et al. |
| 5,782,756 A | 7/1998 | Mannheimer | 5,961,452 A | 10/1999 | Chung et al. |
| 5,782,757 A | 7/1998 | Diab et al. | 5,964,701 A | 10/1999 | Asada et al. |
| 5,782,758 A | 7/1998 | Ausec et al. | 5,971,930 A | 10/1999 | Elghazzawi |
| 5,786,592 A | 7/1998 | Hök | 5,978,691 A | 11/1999 | Mills |
| 5,788,634 A | 8/1998 | Suda et al. | 5,978,693 A | 11/1999 | Hamilton et al. |
| 5,790,729 A | 8/1998 | Pologe et al. | 5,983,120 A | 11/1999 | Groner et al. |
| 5,792,052 A | 8/1998 | Issacson et al. | 5,983,122 A | 11/1999 | Jarman et al. |
| 5,795,292 A | 8/1998 | Lewis et al. | 5,987,343 A | 11/1999 | Kinast |
| 5,797,841 A | 8/1998 | DeLonzor et al. | 5,991,648 A | 11/1999 | Levin |
| 5,800,348 A | 9/1998 | Kaestle | 5,995,855 A | 11/1999 | Kiani et al. |
| 5,800,349 A | 9/1998 | Isaacson et al. | 5,995,856 A | 11/1999 | Mannheimer et al. |
| 5,803,910 A | 9/1998 | Potratz | 5,995,858 A | 11/1999 | Kinast |
| 5,807,246 A | 9/1998 | Sakaguchi et al. | 5,995,859 A | 11/1999 | Takahashi |
| 5,807,247 A | 9/1998 | Merchant et al. | 5,997,343 A | 12/1999 | Mills et al. |
| 5,807,248 A | 9/1998 | Mills | 5,999,834 A | 12/1999 | Wang et al. |
| 5,810,723 A | 9/1998 | Aldrich | 6,002,952 A | 12/1999 | Diab et al. |
| 5,810,724 A | 9/1998 | Gronvall | 6,005,658 A | 12/1999 | Kaluza et al. |
| 5,813,980 A | 9/1998 | Levinson et al. | 6,006,120 A | 12/1999 | Levin |
| 5,817,008 A | 10/1998 | Rafert et al. | 6,011,985 A | 1/2000 | Athan et al. |
| 5,817,009 A | 10/1998 | Rosenheimer et al. | 6,011,986 A | 1/2000 | Diab |
| 5,817,010 A | 10/1998 | Hibl | 6,014,576 A | 1/2000 | Raley et al. |
| 5,818,985 A | 10/1998 | Merchant et al. | 6,018,673 A | 1/2000 | Chin |
| 5,820,550 A | 10/1998 | Polson et al. | 6,018,674 A | 1/2000 | Aronow |
| 5,823,950 A | 10/1998 | Diab et al. | 6,022,321 A | 2/2000 | Amano et al. |
| 5,823,952 A | 10/1998 | Levinson et al. | 6,023,541 A | 2/2000 | Merchant et al. |
| 5,827,179 A | 10/1998 | Lichter et al. | 6,026,312 A | 2/2000 | Shemwell et al. |
| 5,827,182 A | 10/1998 | Raley et al. | 6,026,314 A | 2/2000 | Amerov et al. |
| 5,829,439 A | 11/1998 | Yokosawa et al. | 6,031,603 A | 2/2000 | Fine et al. |
| 5,830,135 A | 11/1998 | Bosque et al. | 6,035,223 A | 3/2000 | Baker, Jr. |
| 5,830,136 A | 11/1998 | DeLonzor et al. | 6,036,642 A | 3/2000 | Diab et al. |
| 5,830,137 A | 11/1998 | Scharf | 6,041,247 A | 3/2000 | Weckstrom et al. |
| 5,839,439 A | 11/1998 | Nierlich et al. | 6,044,283 A | 3/2000 | Fein et al. |
| RE36,000 E | 12/1998 | Swedlow et al. | 6,047,201 A | 4/2000 | Jackson, III |
| 5,842,979 A | 12/1998 | Jarman | 6,055,447 A | 4/2000 | Weil |
| 5,842,981 A | 12/1998 | Larsen et al. | 6,061,584 A | 5/2000 | Lovejoy et al. |
| 5,842,982 A | 12/1998 | Mannheimer | 6,064,898 A | 5/2000 | Aldrich |
| 5,846,190 A | 12/1998 | Woehrle | 6,064,899 A | 5/2000 | Fein et al. |
| 5,851,178 A | 12/1998 | Aronow | 6,067,462 A | 5/2000 | Diab et al. |
| 5,851,179 A | 12/1998 | Ritson et al. | 6,073,038 A | 6/2000 | Wang et al. |
| 5,853,364 A | 12/1998 | Baker, Jr. et al. | 6,078,829 A | 6/2000 | Uchida |
| 5,860,919 A | 1/1999 | Kiani-Azarbayjany et al. | 6,078,833 A | 6/2000 | Hueber |
| 5,865,736 A | 2/1999 | Baker, Jr. et al. | 6,081,735 A | 6/2000 | Diab et al. |
| 5,879,294 A | 3/1999 | Anderson et al. | 6,083,157 A | 7/2000 | Noller |
| 5,885,213 A | 3/1999 | Richardson et al. | 6,083,172 A | 7/2000 | Baker, Jr. et al. |
| 5,890,929 A | 4/1999 | Mills et al. | 6,088,607 A | 7/2000 | Diab et al. |
| 5,891,021 A | 4/1999 | Dillon et al. | 6,094,592 A | 7/2000 | Yorkey et al. |
| 5,891,022 A | 4/1999 | Pologe | 6,095,974 A | 8/2000 | Shemwell et al. |
| 5,891,024 A | 4/1999 | Jarman et al. | 6,104,938 A | 8/2000 | Huiku et al. |
| 5,891,025 A | 4/1999 | Buschmann et al. | 6,104,939 A | 8/2000 | Groner |
| 5,891,026 A | 4/1999 | Wang et al. | 6,112,107 A | 8/2000 | Hannula |
| 5,902,235 A | 5/1999 | Lewis et al. | 6,113,541 A | 9/2000 | Dias et al. |
| 5,910,108 A | 6/1999 | Solenberger | 6,115,621 A | 9/2000 | Chin |
| 5,911,690 A | 6/1999 | Rall | 6,122,535 A | 9/2000 | Kaestle et al. |
| 5,912,656 A | 6/1999 | Tham et al. | 6,133,994 A | 10/2000 | Mathews et al. |
| 5,913,819 A | 6/1999 | Taylor et al. | 6,135,952 A | 10/2000 | Coetzee |
| 5,916,154 A | 6/1999 | Hobbs et al. | 6,144,444 A | 11/2000 | Haworth et al. |
| 5,916,155 A | 6/1999 | Levinson et al. | 6,144,867 A | 11/2000 | Walker et al. |
| 5,919,133 A | 7/1999 | Taylor et al. | 6,144,868 A | 11/2000 | Parker |
| 5,919,134 A | 7/1999 | Diab | 6,149,481 A | 11/2000 | Wang et al. |
| 5,920,263 A | 7/1999 | Huttenhoff et al. | 6,151,107 A | 11/2000 | Schöllerman et al. |
| 5,921,921 A | 7/1999 | Potratz et al. | 6,151,516 A | 11/2000 | Kiani-Azarbayjani et al. |
| 5,922,607 A | 7/1999 | Bernreuter | 6,151,518 A | 11/2000 | Hayashi |
| 5,924,979 A | 7/1999 | Swedlow et al. | 6,152,754 A | 11/2000 | Gerhardt et al. |
| 5,924,980 A | 7/1999 | Coetzee | 6,154,667 A | 11/2000 | Miura |
| 5,924,982 A | 7/1999 | Chin | 6,157,850 A | 12/2000 | Diab et al. |
| 5,924,985 A | 7/1999 | Jones | 6,159,147 A | 12/2000 | Lichter . |
| 5,934,277 A | 8/1999 | Mortz | 6,163,715 A | 12/2000 | Larsen et al. |
| 5,934,925 A | 8/1999 | Tobler et al. | 6,165,005 A | 12/2000 | Mills et al. |
| 5,940,182 A | 8/1999 | Lepper, Jr. et al. | 6,173,196 B1 | 1/2001 | Delonzor et al. |

| | | |
|---|---|---|
| 6,178,343 B1 | 1/2001 | Bindszus et al. |
| 6,179,159 B1 | 1/2001 | Gurley |
| 6,181,958 B1 | 1/2001 | Steuer et al. |
| 6,181,959 B1 | 1/2001 | Schollermann |
| 6,184,521 B1 | 2/2001 | Coffin |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab |
| 6,213,952 B1 | 4/2001 | Finarov |
| 6,217,523 B1 | 4/2001 | Amano et al. |
| 6,222,189 B1 | 4/2001 | Misner et al. |
| 6,223,064 B1 | 4/2001 | Lynn |
| 6,226,539 B1 | 5/2001 | Potratz |
| 6,226,540 B1 | 5/2001 | Bernreuter et al. |
| 6,229,856 B1 | 5/2001 | Diab |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab |
| 6,240,305 B1 | 5/2001 | Tsuchiya |
| 6,253,097 B1 | 6/2001 | Aronow |
| 6,253,098 B1 | 6/2001 | Walker et al. |
| 6,256,523 B1 | 7/2001 | Diab |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab |
| 6,263,223 B1 | 7/2001 | Sheperd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. |
| 6,280,213 B1 | 8/2001 | Tobler |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,330,468 B1 | 12/2001 | Scharf |
| 6,334,065 B1 | 12/2001 | Al-Ali |
| 6,339,715 B1 | 1/2002 | Bahr et al. |
| 6,342,039 B1 | 1/2002 | Lynn |
| 6,343,223 B1 | 1/2002 | Chin et al. |
| 6,343,224 B1 | 1/2002 | Parker |
| 6,349,228 B1 | 2/2002 | Kiani |
| 6,351,658 B1 | 2/2002 | Middleman et al. |
| 6,353,750 B1 | 3/2002 | Kimura |
| 6,356,774 B1 | 3/2002 | Bernstein et al. |
| 6,360,113 B1 | 3/2002 | Dettling |
| 6,360,114 B1 | 3/2002 | Diab |
| 6,361,501 B1 | 3/2002 | Amano et al. |
| 6,363,269 B1 | 3/2002 | Hanna et al. |
| D455,834 S | 4/2002 | Donars et al. |
| 6,370,408 B1 | 4/2002 | Merchant et al. |
| 6,370,409 B1 | 4/2002 | Chung et al. |
| 6,371,921 B1 | 4/2002 | Caro |
| 6,374,129 B1 | 4/2002 | Chin |
| 6,377,829 B1 | 4/2002 | Al-Ali |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz |
| 6,393,310 B1 | 5/2002 | Kuenster |
| 6,393,311 B1 | 5/2002 | Edgar, Jr. et al. |
| 6,397,091 B2 | 5/2002 | Diab |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,400,973 B1 | 6/2002 | Winter |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber |
| 6,434,408 B1 | 8/2002 | Heckel et al. |
| 6,438,396 B1 | 8/2002 | Cook |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic |
| 6,470,200 B2 | 10/2002 | Walker et al. |
| 6,480,729 B2 | 11/2002 | Stone |
| 6,490,466 B1 | 12/2002 | Fein et al. |
| 6,493,568 B1 | 12/2002 | Bell |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills |
| 6,526,300 B1 | 2/2003 | Kiani |
| 6,526,301 B2 | 2/2003 | Larsen et al. |
| 6,541,756 B2 | 4/2003 | Schulz |
| 6,542,764 B1 | 4/2003 | Al-Ali |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,554,788 B1 | 4/2003 | Hunley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz |
| 6,584,336 B1 | 6/2003 | Ali-Ali |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani |
| 6,600,940 B1 | 7/2003 | Fein et al. |
| 6,606,510 B2 | 8/2003 | Swedlow et al. |
| 6,606,511 B1 | 8/2003 | Ali-Ali |

| Patent | Type | Date | Inventor |
|---|---|---|---|
| 6,606,512 | B2 | 8/2003 | Muz et al. |
| 6,609,016 | B1 | 8/2003 | Lynn |
| 6,615,064 | B1 | 9/2003 | Aldrich |
| 6,615,065 | B1 | 9/2003 | Barrett et al. |
| 6,618,602 | B2 | 9/2003 | Levin |
| 6,622,034 | B1 | 9/2003 | Gorski et al. |
| 6,628,975 | B1 | 9/2003 | Fein et al. |
| 6,631,281 | B1 | 10/2003 | Kästle |
| 6,632,181 | B2 | 10/2003 | Flaherty |
| 6,640,116 | B2 | 10/2003 | Diab |
| 6,643,530 | B2 | 11/2003 | Diab |
| 6,643,531 | B1 | 11/2003 | Katarow |
| 6,647,279 | B2 | 11/2003 | Pologue |
| 6,647,280 | B2 | 11/2003 | Bahr et al. |
| 6,650,916 | B2 | 11/2003 | Cook |
| 6,650,917 | B2 | 11/2003 | Diab |
| 6,650,918 | B2 | 11/2003 | Terry |
| 6,654,621 | B2 | 11/2003 | Palatnik |
| 6,654,622 | B1 | 11/2003 | Eberhard et al. |
| 6,654,623 | B1 | 11/2003 | Kästle |
| 6,654,624 | B2 | 11/2003 | Diab |
| 6,658,277 | B2 | 12/2003 | Wassermann |
| 6,658,279 | B1 | 12/2003 | Kiani |
| 6,662,033 | B2 | 12/2003 | Casciani et al. |
| 6,665,551 | B1 | 12/2003 | Suzuki |
| 6,668,182 | B2 | 12/2003 | Hubelbank |
| 6,668,183 | B2 | 12/2003 | Hicks et al. |
| 6,671,526 | B1 | 12/2003 | Aoyagi et al. |
| 6,671,528 | B2 | 12/2003 | Steuer et al. |
| 6,671,530 | B2 | 12/2003 | Chung et al. |
| 6,671,531 | B2 | 12/2003 | Al-Ali |
| 6,671,532 | B1 | 12/2003 | Fudge et al. |
| 6,675,031 | B1 | 1/2004 | Porges et al. |
| 6,678,543 | B2 | 1/2004 | Diab |
| 6,681,126 | B2 | 1/2004 | Solenberger |
| 6,681,128 | B2 | 1/2004 | Steuer et al. |
| 6,681,454 | B2 | 1/2004 | Modgil et al. |
| 6,684,090 | B2 | 1/2004 | Tustin |
| 6,684,091 | B2 | 1/2004 | Parker |
| 6,694,160 | B2 | 2/2004 | Chin |
| 6,697,653 | B2 | 2/2004 | Hanna |
| 6,697,655 | B2 | 2/2004 | Sueppel et al. |
| 6,697,656 | B1 | 2/2004 | Al-Ali |
| 6,697,658 | B2 | 2/2004 | Al-Ali |
| RE38,476 | E | 3/2004 | Diab et al. |
| 6,699,194 | B1 | 3/2004 | Diab |
| 6,699,199 | B2 | 3/2004 | Asada et al. |
| 6,701,170 | B2 | 3/2004 | Stetson |
| 6,702,752 | B2 | 3/2004 | Dekker |
| 6,707,257 | B2 | 3/2004 | Norris |
| 6,708,049 | B1 | 3/2004 | Berson et al. |
| 6,709,402 | B2 | 3/2004 | Dekker |
| 6,711,424 | B1 | 3/2004 | Fine et al. |
| 6,711,425 | B1 | 3/2004 | Reuss |
| 6,712,762 | B1 | 3/2004 | Lichter |
| 6,714,803 | B1 | 3/2004 | Mortz |
| 6,714,804 | B2 | 3/2004 | Al-Ali |
| 6,714,805 | B2 | 3/2004 | Jeon et al. |
| RE38,492 | E | 4/2004 | Diab et al. |
| 6,719,686 | B2 | 4/2004 | Coakley et al. |
| 6,719,705 | B2 | 4/2004 | Mills |
| 6,720,734 | B2 | 4/2004 | Norris |
| 6,721,584 | B2 | 4/2004 | Baker, Jr. et al. |
| 6,721,585 | B1 | 4/2004 | Parker |
| 6,725,074 | B1 | 4/2004 | Kästle |
| 6,725,075 | B2 | 4/2004 | Al-Ali |
| 6,731,962 | B1 | 5/2004 | Katarow |
| 6,731,963 | B2 | 5/2004 | Finarov et al. |
| 6,731,967 | B1 | 5/2004 | Turcott |
| 6,735,459 | B2 | 5/2004 | Parker |
| 6,745,060 | B2 | 6/2004 | Diab et al. |
| 6,745,061 | B1 * | 6/2004 | Hicks et al. .................. 600/344 |
| 6,748,253 | B2 | 6/2004 | Norris et al. |
| 6,748,254 | B2 | 6/2004 | O'Neill et al. |
| 6,754,515 | B1 | 6/2004 | Pologe |
| 6,754,516 | B2 | 6/2004 | Mannheimer |
| 6,760,607 | B2 | 7/2004 | Al-Ali |
| 6,760,609 | B2 | 7/2004 | Jacques |
| 6,760,610 | B2 | 7/2004 | Tscupp et al. |
| 6,763,255 | B2 | 7/2004 | DeLonzor et al. |
| 6,763,256 | B2 | 7/2004 | Kimball et al. |
| 6,770,028 | B1 | 8/2004 | Ali et al. |
| 6,771,994 | B2 | 8/2004 | Kiani et al. |
| 6,773,397 | B2 | 8/2004 | Kelly |
| 6,778,923 | B2 | 8/2004 | Norris et al. |
| 6,780,158 | B2 | 8/2004 | Yarita |
| 6,791,689 | B1 | 9/2004 | Weckstrom |
| 6,792,300 | B1 | 9/2004 | Diab |
| 6,801,797 | B2 | 10/2004 | Mannheimer et al. |
| 6,801,798 | B2 | 10/2004 | Geddes et al. |
| 6,801,799 | B2 | 10/2004 | Mendelson |
| 6,801,802 | B2 | 10/2004 | Sitzman et al. |
| 6,802,812 | B1 | 10/2004 | Walker et al. |
| 6,805,673 | B2 | 10/2004 | Dekker |
| 6,810,277 | B2 | 10/2004 | Edgar, Jr. et al. |
| 6,813,511 | B2 | 11/2004 | Diab |
| 6,816,741 | B2 | 11/2004 | Diab |
| 6,819,950 | B2 | 11/2004 | Mills |
| 6,822,564 | B2 | 11/2004 | Al-Ali |
| 6,825,619 | B2 | 11/2004 | Norris |
| 6,826,419 | B2 | 11/2004 | Diab et al. |
| 6,829,496 | B2 | 12/2004 | Nagai et al. |
| 6,830,711 | B2 | 12/2004 | Mills |
| 6,836,679 | B2 | 12/2004 | Baker, Jr. et al. |
| 6,839,579 | B1 | 1/2005 | Chin |
| 6,839,580 | B2 | 1/2005 | Zonios et al. |
| 6,839,582 | B2 | 1/2005 | Heckel |
| 6,839,659 | B2 | 1/2005 | Tarassenko et al. |
| 6,842,635 | B1 | 1/2005 | Parker |
| 6,845,256 | B2 | 1/2005 | Chin |
| 6,850,787 | B2 | 2/2005 | Weber et al. |
| 6,850,788 | B2 | 2/2005 | Al-Ali |
| 6,850,789 | B2 | 2/2005 | Schweitzer, Jr. et al. |
| 6,861,639 | B2 | 3/2005 | Al-Ali |
| 6,863,652 | B2 | 3/2005 | Huang et al. |
| 6,865,407 | B2 | 3/2005 | Kimball et al. |
| 6,879,850 | B2 | 4/2005 | Kimball |
| 6,882,874 | B2 | 4/2005 | Huiku |
| 6,898,452 | B2 | 5/2005 | Al-Ali et al. |
| 6,909,912 | B2 | 6/2005 | Melker |
| 6,912,413 | B2 | 6/2005 | Rantala et al. |
| 6,916,289 | B2 | 7/2005 | Schnall |
| 6,920,345 | B2 | 7/2005 | Al-Ali et al. |
| 6,931,269 | B2 | 8/2005 | Terry |
| 6,934,570 | B2 | 8/2005 | Kiani et al. |
| 6,941,162 | B2 | 9/2005 | Fudge et al. |
| 6,947,781 | B2 | 9/2005 | Asada et al. |
| 6,950,687 | B2 | 9/2005 | Al-Ali |
| 6,954,664 | B2 | 10/2005 | Sweitzer |
| 6,963,767 | B2 | 11/2005 | Rantala et al. |
| 6,968,221 | B2 | 11/2005 | Rosenthal |
| 6,971,580 | B2 | 12/2005 | DeLonzor et al. |
| 6,979,812 | B2 | 12/2005 | Al-Ali |
| 6,983,178 | B2 | 1/2006 | Fine |
| 6,985,763 | B2 | 1/2006 | Boas et al. |
| 6,985,764 | B2 | 1/2006 | Mason |
| 6,990,426 | B2 | 1/2006 | Yoon et al. |
| 6,992,751 | B2 | 1/2006 | Al-Ali |
| 6,992,772 | B2 | 1/2006 | Block et al. |
| 6,993,371 | B2 | 1/2006 | Kiani et al. |
| 6,993,372 | B2 | 1/2006 | Fine et al. |
| 6,996,427 | B2 | 2/2006 | Ali et al. |
| 7,003,338 | B2 | 2/2006 | Weber et al. |
| 7,003,339 | B2 | 2/2006 | Diab et al. |
| 7,006,855 | B1 | 2/2006 | Sarussi |
| 7,006,856 | B2 | 2/2006 | Baker, Jr. et al. |

| | | |
|---|---|---|
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker |
| 7,025,728 B2 | 4/2006 | Ito et al. |
| 7,027,849 B2 | 4/2006 | Al-Ali et al. |
| 7,027,850 B2 | 4/2006 | Wasserman |
| 7,039,449 B2 | 5/2006 | Al-Ali |
| 7,043,289 B2 | 5/2006 | Fine et al. |
| 7,047,055 B2 | 5/2006 | Boaz et al. |
| 7,060,035 B2 | 6/2006 | Wasserman et al. |
| 7,062,307 B2 | 6/2006 | Norris et al. |
| 7,067,893 B2 | 6/2006 | Mills |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker |
| 7,130,671 B2 | 10/2006 | Baker, Jr. et al. |
| 7,132,641 B2 | 11/2006 | Schulz |
| 7,133,711 B2 | 11/2006 | Chernoguz et al. |
| 7,139,599 B2 | 11/2006 | Terry |
| 7,142,901 B2 | 11/2006 | Kiani et al. |
| 7,162,288 B2 | 1/2007 | Nordstrom et al. |
| 7,190,987 B2 | 3/2007 | Lindekugel et al. |
| 7,198,778 B2 | 4/2007 | Mannheimer et al. |
| 7,215,984 B2 | 5/2007 | Diab et al. |
| 7,225,006 B2 | 5/2007 | Al-Ali et al. |
| 7,228,161 B2 | 6/2007 | Chin |
| 7,236,811 B2 | 6/2007 | Schmitt et al. |
| 7,248,910 B2 | 7/2007 | Li et al. |
| 7,254,433 B2 | 8/2007 | Diab et al. |
| 7,254,434 B2 | 8/2007 | Schulz et al. |
| 7,280,858 B2 | 10/2007 | Al-Ali et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 7,412,272 B2 | 8/2008 | Medina |
| 2001/0021803 A1 | 9/2001 | Blank et al. |
| 2001/0051767 A1 | 12/2001 | Williams et al. |
| 2002/0016537 A1 | 2/2002 | Muz et al. |
| 2002/0026109 A1 | 2/2002 | Diab et al. |
| 2002/0028990 A1 | 3/2002 | Sheperd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0072681 A1 | 6/2002 | Schnall |
| 2002/0116797 A1 | 8/2002 | Modgil et al. |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0107065 A1 | 6/2004 | Al-Ali et al. |
| 2004/0116788 A1 | 6/2004 | Chernoguz et al. |
| 2004/0116789 A1 | 6/2004 | Boaz et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0167381 A1 | 8/2004 | Lichter |
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0215085 A1 | 10/2004 | Schnall |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0014999 A1 | 1/2005 | Rahe-Meyer |
| 2005/0020887 A1 | 1/2005 | Goldberg |

| | | | | | |
|---|---|---|---|---|---|
| 2005/0020894 A1 | 1/2005 | Norris et al. | EP | 00724860 | 8/1996 |
| 2005/0033128 A1 | 2/2005 | Ali et al. | EP | 00793942 | 9/1997 |
| 2005/0033129 A1 | 2/2005 | Edgar, Jr. et al. | EP | 0 864 293 A1 | 9/1998 |
| 2005/0033131 A1 | 2/2005 | Chen | EP | 01006863 | 10/1998 |
| 2005/0043599 A1 | 2/2005 | O'Mara | EP | 01006864 | 10/1998 |
| 2005/0043600 A1 | 2/2005 | Diab | EP | 0875199 | 11/1998 |
| 2005/0049468 A1 | 3/2005 | Carlson | EP | 00998214 | 12/1998 |
| 2005/0049470 A1 | 3/2005 | Terry | EP | 0 898 933 A | 3/1999 |
| 2005/0049471 A1 | 3/2005 | Aceti | EP | 0 898 933 A2 | 3/1999 |
| 2005/0070773 A1 | 3/2005 | Chin | EP | 01332713 | 8/2003 |
| 2005/0070775 A1 | 3/2005 | Chin | EP | 01469773 | 8/2003 |
| 2005/0075546 A1 | 4/2005 | Samsoondar | EP | 1502529 | 7/2004 |
| 2005/0075550 A1 | 4/2005 | Lindekugel | EP | 01491135 | 12/2004 |
| 2005/0085704 A1 | 4/2005 | Schulz | EP | 1491135 | 12/2004 |
| 2005/0090720 A1 | 4/2005 | Wu | EP | 1807001 | 7/2007 |
| 2005/0197548 A1 | 9/2005 | Dietiker | FR | 2685865 | 1/1992 |
| 2005/0228248 A1 | 10/2005 | Dietiker | GB | 2 259 545 A | 3/1993 |
| 2005/0234317 A1 | 10/2005 | Kiani | JP | 63275325 | 11/1988 |
| 2005/0256386 A1 | 11/2005 | Chan et al. | JP | 2013450 | 1/1990 |
| 2005/0272986 A1 | 12/2005 | Smith | JP | 2111343 | 4/1990 |
| 2005/0277819 A1 | 12/2005 | Kiani et al. | JP | 02-191434 | 7/1990 |
| 2006/0020179 A1 | 1/2006 | Anderson | JP | 2237544 | 9/1990 |
| 2006/0030764 A1 | 2/2006 | Porges | JP | 03-173536 | 7/1991 |
| 2006/0058594 A1 | 3/2006 | Ishizuka et al. | JP | 3170866 | 7/1991 |
| 2006/0074280 A1 | 4/2006 | Martis | JP | 3245042 | 10/1991 |
| 2006/0084852 A1 | 4/2006 | Mason et al. | JP | 4038280 | 3/1992 |
| 2006/0084878 A1 | 4/2006 | Banet | JP | 4174648 | 6/1992 |
| 2006/0089547 A1 | 4/2006 | Sarussi | JP | 4191642 | 7/1992 |
| 2006/0106294 A1 | 5/2006 | Maser et al. | JP | 4332536 | 11/1992 |
| 2006/0122517 A1 | 6/2006 | Banet | JP | 3124073 | 3/1993 |
| 2006/0129039 A1 | 6/2006 | Lindner | JP | 5049624 | 3/1993 |
| 2006/0155198 A1 | 7/2006 | Schmid | JP | 5049625 | 3/1993 |
| 2006/0173257 A1 | 8/2006 | Nagai | JP | 3115374 | 4/1993 |
| 2006/0200029 A1 | 9/2006 | Evans et al. | JP | 05-200031 | 8/1993 |
| | | | JP | 5212016 | 8/1993 |
| FOREIGN PATENT DOCUMENTS | | | JP | 06-014906 | 1/1994 |
| DE | 3405444 A1 | 8/1985 | JP | 6016774 | 3/1994 |
| DE | 3516338 A1 | 11/1986 | JP | 3116255 | 4/1994 |
| DE | 37 03 458 C2 | 8/1988 | JP | 6029504 | 4/1994 |
| DE | 3938759 A1 | 5/1991 | JP | 6098881 | 4/1994 |
| DE | 4210102 | 9/1993 | JP | 06-154177 | 6/1994 |
| DE | 44 23 597 C1 | 8/1995 | JP | 6269430 | 9/1994 |
| DE | 4423597 C1 | 8/1995 | JP | 6285048 | 10/1994 |
| DE | 19632361 A1 | 2/1997 | JP | 7001273 | 1/1995 |
| DE | 69123448 T2 | 5/1997 | JP | 7124138 | 5/1995 |
| DE | 19703220 A1 | 7/1997 | JP | 7136150 | 5/1995 |
| DE | 19640807 | 9/1997 | JP | 3116259 | 6/1995 |
| DE | 19647877 | 4/1998 | JP | 3116260 | 6/1995 |
| DE | 100 30 862 | 1/2002 | JP | 7155311 | 6/1995 |
| DE | 20318882 | 4/2004 | JP | 7155313 | 6/1995 |
| EP | 0127947 | 5/1984 | JP | 3238813 | 7/1995 |
| EP | 00194105 | 9/1986 | JP | 7171139 | 7/1995 |
| EP | 0 204 459 A2 | 12/1986 | JP | 3134144 | 9/1995 |
| EP | 0204 459 | 12/1986 | JP | 7236625 | 9/1995 |
| EP | 204459 | 12/1986 | JP | 7246191 | 9/1995 |
| EP | 0 262 779 A1 | 4/1988 | JP | 8256996 | 10/1996 |
| EP | 0315040 | 10/1988 | JP | 9192120 | 7/1997 |
| EP | 0314331 | 5/1989 | JP | 10216113 | 8/1998 |
| EP | 00352923 | 1/1990 | JP | 10216114 | 8/1998 |
| EP | 0 360 977 A1 | 4/1990 | JP | 10216115 | 8/1998 |
| EP | 430340 | 6/1991 | JP | 10337282 | 12/1998 |
| EP | 00430340 | 6/1991 | JP | 11019074 | 1/1999 |
| EP | 0435 500 | 7/1991 | JP | 11155841 | 6/1999 |
| EP | 00497021 | 8/1992 | JP | 11-188019 | 7/1999 |
| EP | 0529412 | 8/1992 | JP | 11244268 | 9/1999 |
| EP | 0531631 | 9/1992 | JP | 20107157 | 4/2000 |
| EP | 0566354 | 4/1993 | JP | 20237170 | 9/2000 |
| EP | 0587009 | 8/1993 | JP | 21245871 | 9/2001 |
| EP | 00630203 | 9/1993 | JP | 22224088 | 8/2002 |
| EP | 0 572 684 A1 | 12/1993 | JP | 22282242 | 10/2002 |
| EP | 00615723 | 9/1994 | JP | 23153881 | 5/2003 |
| EP | 00702931 | 3/1996 | JP | 23153882 | 5/2003 |
| | | | JP | 23169791 | 6/2003 |

| | | |
|---|---|---|
| JP | 23194714 | 7/2003 |
| JP | 23210438 | 7/2003 |
| JP | 23275192 | 9/2003 |
| JP | 23339678 | 12/2003 |
| JP | 24008572 | 1/2004 |
| JP | 24089546 | 3/2004 |
| JP | 24113353 | 4/2004 |
| JP | 24135854 | 5/2004 |
| JP | 24148069 | 5/2004 |
| JP | 24148070 | 5/2004 |
| JP | 24159810 | 6/2004 |
| JP | 24166775 | 6/2004 |
| JP | 24194908 | 7/2004 |
| JP | 24202190 | 7/2004 |
| JP | 24248820 | 9/2004 |
| JP | 24261364 | 9/2004 |
| JP | 24290412 | 10/2004 |
| JP | 24290544 | 10/2004 |
| JP | 24290545 | 10/2004 |
| JP | 24329406 | 11/2004 |
| JP | 24329607 | 11/2004 |
| JP | 24329928 | 11/2004 |
| JP | 24337605 | 12/2004 |
| JP | 24344367 | 12/2004 |
| JP | 24351107 | 12/2004 |
| JP | 25034472 | 2/2005 |
| JP | 25110816 | 4/2005 |
| JP | 26158555 | 6/2006 |
| WO | WO 98/09566 | 10/1989 |
| WO | WO 90/01293 | 2/1990 |
| WO | WO 90/04352 | 5/1990 |
| WO | WO 91/01678 | 2/1991 |
| WO | WO 91/11137 | 8/1991 |
| WO | WO 92/00513 | 1/1992 |
| WO | WO 92/21281 | 12/1992 |
| WO | WO 93/09711 | 5/1993 |
| WO | WO 93/13706 | 7/1993 |
| WO | WO 93/16629 | 9/1993 |
| WO | WO 94/03102 | 2/1994 |
| WO | WO 94/23643 | 10/1994 |
| WO | WO 95/02358 | 1/1995 |
| WO | WO 95/12349 | 5/1995 |
| WO | WO 95/16970 | 6/1995 |
| WO | WO 96/13208 | 5/1996 |
| WO | WO 96/39927 | 12/1996 |
| WO | WO 97/36536 | 10/1997 |
| WO | WO 97/36538 | 10/1997 |
| WO | WO 97/40741 | 11/1997 |
| WO | WO 97/49330 | 12/1997 |
| WO | WO 98/17174 | 4/1998 |
| WO | WO 98/18382 | 5/1998 |
| WO | WO 98/43071 | 10/1998 |
| WO | WO 98/51212 | 11/1998 |
| WO | WO 98/57577 | 12/1998 |
| WO | WO 99/00053 | 1/1999 |
| WO | WO 99/32030 | 7/1999 |
| WO | WO 99/47039 | 9/1999 |
| WO | WO 99/63884 | 12/1999 |
| WO | WO 00/21438 | 4/2000 |
| WO | WO 00/28888 | 5/2000 |
| WO | 0059374 | 10/2000 |
| WO | WO 00/59374 | 10/2000 |
| WO | WO 00/47426 | 3/2001 |
| WO | WO 01/13790 | 3/2001 |
| WO | WO 01/16577 | 3/2001 |
| WO | WO 01/17421 | 3/2001 |
| WO | WO 01/40776 | 6/2001 |
| WO | WO 01/67946 A1 | 9/2001 |
| WO | WO 01/76461 | 10/2001 |
| WO | WO 02/14793 | 2/2002 |
| WO | WO 02/35999 | 5/2002 |
| WO | WO 02/062213 | 8/2002 |
| WO | WO 02/074162 | 9/2002 |
| WO | WO 02/085202 A1 | 10/2002 |
| WO | WO 03/000125 | 1/2003 |
| WO | WO 03/001180 | 1/2003 |
| WO | WO 03/009750 | 2/2003 |
| WO | WO 03/011127 | 2/2003 |
| WO | WO 03/020129 A1 | 3/2003 |
| WO | WO 03/039326 | 5/2003 |
| WO | WO 03/063697 | 8/2003 |
| WO | WO 03/073924 | 9/2003 |
| WO | WO 2004/000114 | 12/2003 |
| WO | WO 2004/006748 | 1/2004 |
| WO | WO 2004/069046 A1 | 8/2004 |
| WO | WO 2004/075746 | 9/2004 |
| WO | WO 2005/002434 | 1/2005 |
| WO | WO 2005/009221 | 2/2005 |
| WO | WO 2005/010567 | 2/2005 |
| WO | WO 2005/010568 | 2/2005 |
| WO | WO 2005/020120 | 3/2005 |
| WO | WO 2005/065540 A1 | 7/2005 |
| WO | 06064399 | 6/2006 |
| WO | WO 2006/104790 | 10/2006 |

OTHER PUBLICATIONS

Azhar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate" *Respiratory Care*, vol. 42, No. 1, p. 1072 (Nov. 1997).

Poets, C.F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30-Nov. 2, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

"Smaller Product, Tighter Tolerances Pose Dispensing Challenges for Medical Device Manufacturer," *Adhesives Age*, pp. 40-41 (Oct. 1997).

Buschman, J.P., et al.; "Principles and Problems of Calibration of Fetal Oximeters," *Biomedizinische Technik*, vol. 42, pp. 265-266 (1997).

Pickett, John, et al.; "Pulse Oximetry and PPG Measurements in Plastic Surgery," *Proceedings— 19th International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

Dekock, Marc; "Pulse Oximetry Probe Adhesive Disks: a Potential for Infant Aspiration," *Anesthesiology*, vol. 89, pp. 1603-1604 (1998).

East, Christine E., et al.; "Fetal Oxygen Saturation and Uterine Contractions During Labor," *American Journal of Perinatology*, vol. 15, No. 6, pp. 345-349 (Jun. 1998).

Rhee, Sokwoo et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1909 (Oct. 1998).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich System," *Journal of Clinical Monitoring and Computing*, vol. 14, pp. 403-412 (1998).

Nogawa, Masamichi, et al.; "A Novel Hybrid Reflectance Pulse Oximater Sensor with improved Linearity and General Applicability to Various Portions of the Body," *Proceedings of the 20th Annual International Conference of the IEEE Engineering in Medicine and Biology Society*, vol. 20, No. 4, pp. 1858-1861 (1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engineering in Medicine and Biology Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle S.; "An Algorithm for Reliable Processing of Pulse Oximetry Signals Under strong Noise Conditions," *Dissertation Book*, Lubeck University, Germany (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796-2799.

Vicenzi, Martin N.; "Transesophageal versus surface pulse oximetry in intensive care unit patients," *Crit. Care Med.*; vol. 28, No. 7, pp. 2268-2270 (2000).

Goldman. Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved In Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al., "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al., "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; " Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *PhysioL Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Lopez-Sliva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmogaphic Recording using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya, Yoshiki, et al.; "Validity of pulse oximetry during maximal exercise in normoxia, hypoxia, and hyperoxia," *J. Appl. Physiol*, vol. 92, pp. 162-168 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou. P. A., et al.; "Investigation of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al., "In vivo application of a minimally invasive oximetry based perfusion sensor," *Proceedings of the Second Joint EMBS/BMES Conference*, Houston, Texas; Oct. 23-26, 2002; pp. 1789-1790.

Yoon, Gilwon, et al.; "Multiple diagnosis based on Photoplethysmography: hematocrib, SpO2, pulse and respiration," *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisarn, W., et al.; "A non-invasive hemoglobin measurement based pulse oximetry," *Optics in Health Care and Biomedical Optics: Diagnostics and Treatment; Proceedings of SPIE*, vol. 4916; pp. 489-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2001).

Lopez-Sliva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the $25^{th}$ Annual International Conference of the IEEE EMBS*, Cancun, Mexico, Sep. 17-21, 2003, pp. 2439-2442.

Matthews, Nora S. et al.; "An evaluation of pulse oximeters in dogs, cats and horses," *Veterinary Anaesthesa and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Mendelson, Y., et al.; "Measurement Site and Photodetector Size Considerations in Optimizing Power Consumption a Wearable Reflectance Pulse Oximeter," *Proceedings of the $25^{th}$ Annual International conference of the IEEE EMBS*, Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using a Miniature earlobe sensor," *Jinko Kokyo (Aritificial Respiration)*, vol. 20, No. 1, pp. 24-29(2003).

Lebak, J.W., et al.; "Implementation of a Standards-Based Pulse Oximeter on a Wearable, Embedded Platform," *Proceeding of the $25^{th}$ Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceeding of the $25^{th}$ Annual International Conference of the IEEE EMBS*, Cancun, Mexico, Sep. 17-21, 2008; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the $25^{th}$ Annual International Conference of the IEEE EMBS*, Cancun, Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

Johansson; A. "Neural network for photoplethysmographic respiratory rate monitoring," *Medical & Biological Engineering & Computing*, vol. 41, pp. 242-248 (2003).

Reuss, James. L.; "Factors Influencing Fetal Pulse Oximetry Performance," *Journal of clinical and Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Sugino, Shigekzau, et al.; "Forehead is as sensitive as finger pulse oximetry during general anesthesia," *Can J. Anesth; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor,", *Proceedings o the 26$^{th}$ Annual International conference of the IEEE EMBS*, San Francisco, California, Sep. 1-5, 2004, pp. 4759-4762.

Kocher, Serge, et al.; "Performance of a Digital $PCO_2/SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26$^{th}$ Annual International conference of the IEEE EMBS*, San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia*, vol. 59, pp. 390-393 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the 26$^{th}$ Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

* cited by examiner

FIG. 4
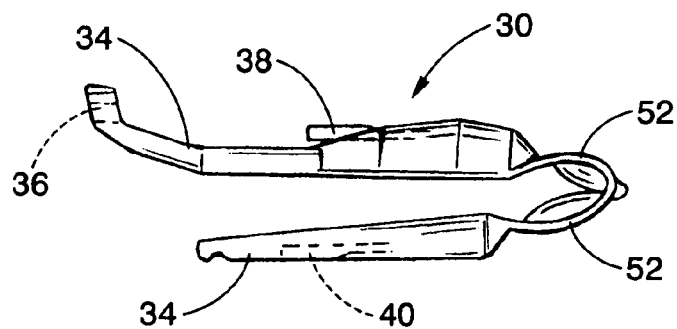
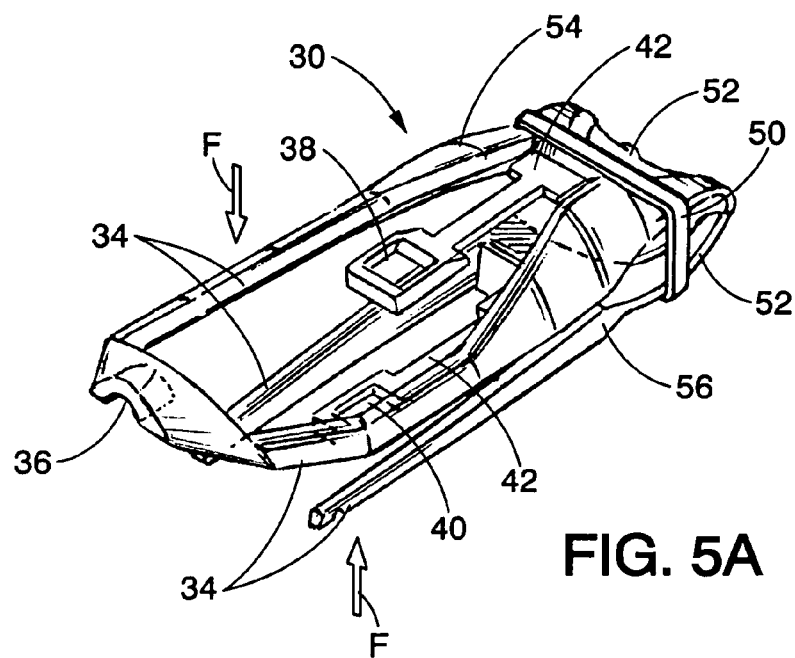
FIG. 5A
FIG. 5B
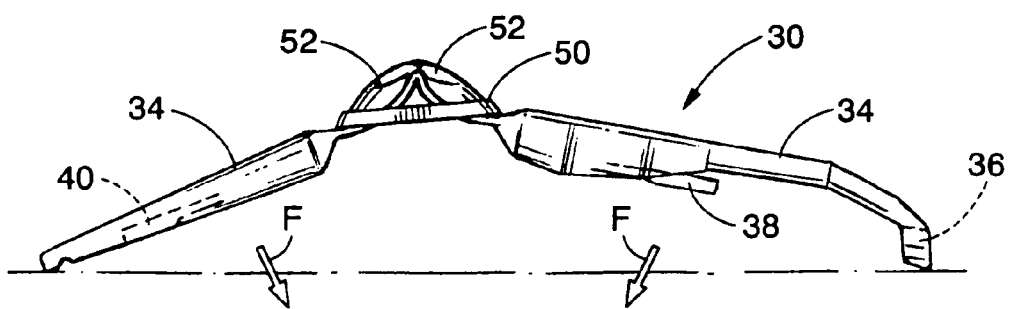

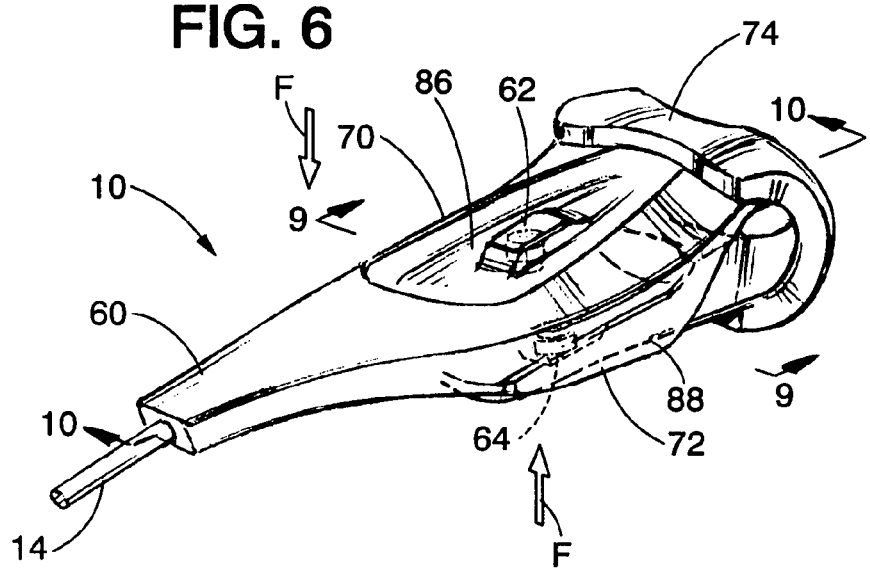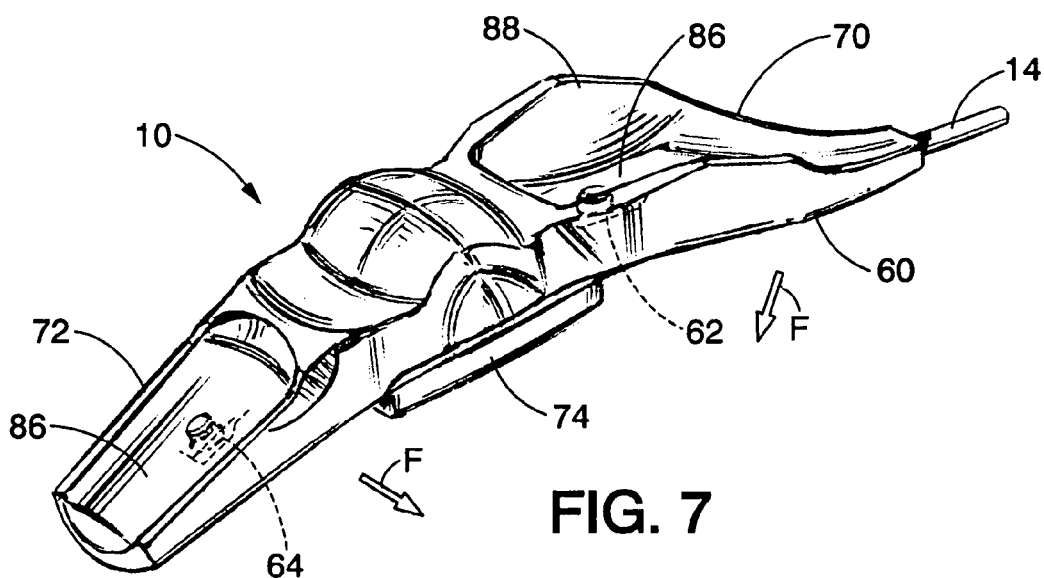

UNITARY MEDICAL SENSOR ASSEMBLY AND TECHNIQUE FOR USING THE SAME

CROSS-REFERENCE TO RELATED APPLICATION

This application is a continuation of U.S. application Ser. No. 11/199,525 filed Aug. 8, 2005, the disclosure of which is hereby incorporated by reference in its entirety.

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximeters typically utilize a non-invasive sensor that is placed on or against a patient's tissue that is well perfused with blood, such as a patient's finger, toe, forehead or earlobe. The pulse oximeter sensor emits light and photoelectrically senses the absorption and/or scattering of the light after passage through the perfused tissue. The data collected by the sensor may then be used to calculate one or more of the above physiological characteristics based upon the absorption or scattering of the light. More specifically, the emitted light is typically selected to be of one or more wavelengths that are absorbed or scattered in an amount related to the presence of oxygenated versus de-oxygenated hemoglobin in the blood. The amount of light absorbed and/or scattered may then be used to estimate the amount of the oxygen in the tissue using various algorithms.

In many instances, it may be desirable to employ, for cost and/or convenience, a pulse oximeter sensor that is reusable. Such reusable sensors, however, may be uncomfortable for the patient for various reasons. For example, the materials used in their construction may not be adequately compliant or supple or the structural features may include angles or edges.

Furthermore, the reusable sensor should fit snugly enough that incidental patient motion will not dislodge or move the sensor, yet not so tight that it may interfere with pulse oximetry measurements. Such a conforming fit may be difficult to achieve over a range of patient physiologies without adjustment or excessive attention on the part of medical personnel. In addition, lack of a tight or secure fit may allow light from the environment to reach the photodetecting elements of the sensor. Such environmental light is not related to a physiological characteristic of the patient and may, therefore, introduce error into the measurements derived using data obtained with the sensor.

Reusable pulse oximeter sensors are also used repeatedly and, typically, on more than one patient. Therefore, over the life of the sensor, detritus and other bio-debris (sloughed off skin cells, dried fluids, dirt, and so forth) may accumulate on the surface of the sensor or in crevices and cavities of the sensor, after repeated uses. As a result, it may be desirable to quickly and/or routinely clean the sensor in a thorough manner. However, in sensors having a multi-part construction, as is typical in reusable pulse oximeter sensors, it may be difficult to perform such a quick and/or routine cleaning. For example, such a thorough cleaning may require disassembly of the sensor and individual cleaning of the disassembled parts or may require careful cleaning using utensils capable of reaching into cavities or crevices of the sensor. Such cleaning is labor intensive and may be impractical in a typical hospital or clinic environment.

SUMMARY

Certain aspects commensurate in scope with the originally claimed invention are set forth below. It should be understood that these aspects are presented merely to provide the reader with a brief summary of certain forms of the invention might take and that these aspects are not intended to limit the scope of the invention. Indeed, the invention may encompass a variety of aspects that may not be set forth below.

There is provided a sensor assembly that includes: a frame comprising a first portion and a second portion connected by a hinge; an emitter disposed on the frame; a detector disposed on the frame; a coating provided over the frame, the emitter, and the detector to form a unitary sensor assembly; and a resistance-providing component disposed generally about the hinge.

There is also provided a method of manufacturing a sensor that includes: positioning an emitter and detector relative to a frame comprising a first portion and a second portion connected by a hinge; and coating the frame, the emitter, and the detector to form a unitary sensor assembly.

There is also included a method for cleaning a sensor assembly that includes: immersing or rinsing a fluid-tight sensor assembly in at least one of water or a disinfectant, wherein electrical and optical components of the fluid-tight sensor assembly are not exposed to the water or the disinfectant during the immersion or rinse.

BRIEF DESCRIPTION OF THE DRAWINGS

Advantages of the invention may become apparent upon reading the following detailed description and upon reference to the drawings in which:

FIG. 4 illustrates a side view of the internal frame of FIG. 2 in a closed configuration;

FIG. 5A illustrates a side view of the internal frame of FIG. 2 in a closed configuration with an elastic band disposed about the hinge region;

FIG. 5B illustrates a side view of the internal frame of FIG. 2 in an open configuration with an elastic band disposed about the hinge region;

FIG. 6 illustrates an overmolded bi-stable sensor, in accordance with aspects of the present technique;

FIG. 7 illustrates the overmolded bi-stable sensor of FIG. 6 in an open configuration;

DETAILED DESCRIPTION OF SPECIFIC EMBODIMENTS

Figure 1:
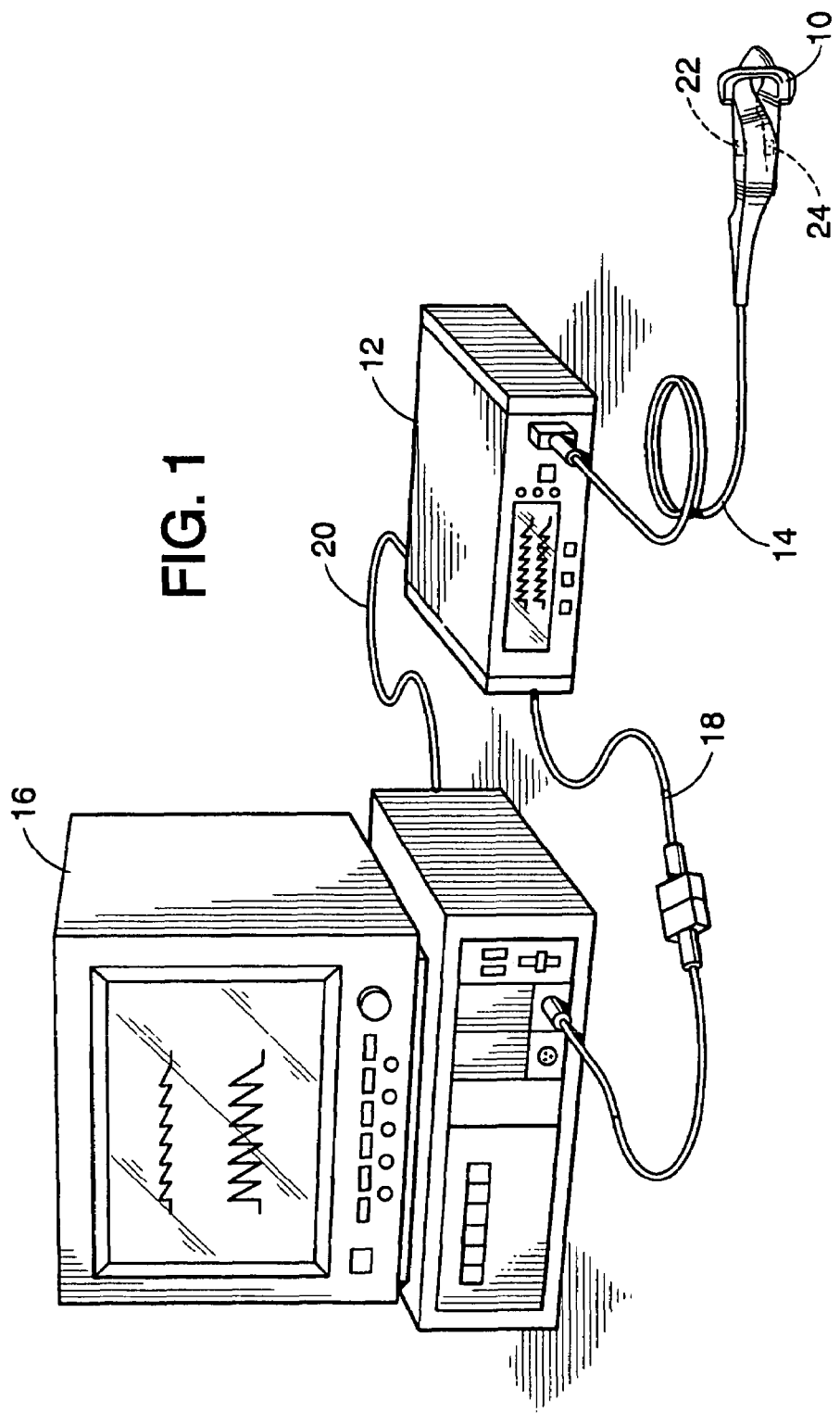
FIG. 1 illustrates a patient monitoring system coupled to a multi-parameter patient monitor and a bi-stable sensor, in accordance with aspects of the present technique.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide a comfortable and conformable reusable patient sensor, such as for use in pulse oximetry or other applications utilizing spectrophotometry, that is easily cleaned and that is resistant to environmental light infiltration. In accordance with some aspects of the present technique, a reusable patient sensor is provided that is overmolded to provide patient comfort and a suitably conformable fit. The overmold material provides a seal against bodily fluids, as well as water or other cleaning fluids, that allows easy cleaning without disassembly or special tools.

In accordance with some aspects of the present technique, the reusable patient sensor has more than one mechanically stable configuration, such as two-stable configurations, in a mechanically bi-stable implementation. As will be appreciated by those of ordinary skill in the art, such multi- or bi-stable configurations are resistant to transitions or movement between stable configurations, therefore each configuration is stable absent an applied force sufficient to overcome this resistance. In this way, a bi-stable device in one of its stable configurations will remain in that stable configuration until a force is applied to overcome the resistance to the transition to the second stable configuration. Once such a force is applied, however, and the bi-stable device is in the second stable configuration, the resistance now functions to resist transition back to the first stable configuration. For example, for a bi-stable sensor having open and closed configurations, the sensor will remain open until sufficient force is applied to close the sensor, however, once closed, the sensor will remain closed absent a second application of force sufficient to re-open the sensor.

Prior to discussing such exemplary multi- or bi-stable sensors in detail, it should be appreciated that such sensors may be designed for use with a typical patient monitoring system. For example, referring now to FIG. 1, a bi-stable sensor 10 according to the present invention may be used in conjunction with a patient monitor 12. In the depicted embodiment, a cable 14 connects the bi-stable sensor 10 to the patient monitor 12. As will be appreciated by those of ordinary skill in the art, the sensor 10 and/or the cable 14 may include or incorporate one or more integrated circuit devices or electrical devices, such as a memory, processor chip, or resistor, that may facilitate or enhance communication between the bi-stable sensor 10 and the patient monitor 12. Likewise the cable 14 may be an adaptor cable, with or without an integrated circuit or electrical device, for facilitating communication between the bi-stable sensor 10 and various types of monitors, including older or newer versions of the patient monitor 12 or other physiological monitors. In other embodiments, the bi-stable sensor 10 and the patient monitor 12 may communicate via wireless means, such as using radio, infrared, or optical signals. In such embodiments, a transmission device (not shown) may be connected to the bi-stable sensor 10 to facilitate wireless transmission between the bi-stable sensor 10 and the patient monitor 12. As will be appreciated by those of ordinary skill in the art, the cable 14 (or corresponding wireless transmissions) are typically used to transmit control or timing signals from the monitor 12 to the bi-stable sensor 10 and/or to transmit acquired data from the bi-stable sensor 10 to the monitor 12. In some embodiments, however, the cable 14 may be an optical fiber that allows optical signals to be conducted between the monitor 12 and the bi-stable sensor 10.

In one embodiment, the patient monitor 12 may be a suitable pulse oximeter, such as those available from Nellcor Puritan Bennett Inc. In other embodiments, the patient monitor 12 may be a monitor suitable for measuring tissue water fractions, or other body fluid related metrics, using spectrophotometric or other techniques. Furthermore, the monitor 12 may be a multi-purpose monitor suitable for performing pulse oximetry and measurement of tissue water fraction, or other combinations of physiological and/or biochemical monitoring processes, using data acquired via the sensor 10. Furthermore, to upgrade conventional monitoring functions provided by the monitor 12 to provide additional functions, the patient monitor 12 may be coupled to a multi-parameter patient monitor 16 via a cable 18 connected to a sensor input port and/or via a cable 20 connected to a digital communication port.

The sensor 10, in the example depicted in FIG. 1, is a bi-stable sensor that is overmolded to provide a unitary or enclosed assembly. The bi-stable sensor 10 includes an emitter 22 and a detector 24 which may be of any suitable type. For example, the emitter 22 may be one or more light emitting diodes adapted to transmit one or more wavelengths of light, such as in the red to infrared range, and the detector 24 may be a photodetector, such as a silicon photodiode package, selected to receive light in the range emitted from the emitter 22. In the depicted embodiment, the bi-stable sensor 10 is coupled to a cable 14 that is responsible for transmitting electrical and/or optical signals to and from the emitter 22 and detector 24 of the bi-stable sensor 10. The cable 14 may be permanently coupled to the bi-stable sensor 10, or it may be removably coupled to the bi-stable sensor 10—the latter alternative being more useful and cost efficient in situations where the bi-stable sensor 10 is disposable.

The bi-stable sensor 10 described above is generally configured for use as a "transmission type" sensor for use in spectrophotometric applications, though in some embodiments it may instead be configured for use as a "reflectance type sensor." Transmission type sensors include an emitter and detector that are typically placed on opposing sides of the sensor site. If the sensor site is a fingertip, for example, the bi-stable sensor 10 is positioned over the patient's fingertip such that the emitter and detector lie on either side of the patient's nail bed. For example, the bi-stable sensor 10 is positioned so that the emitter is located on the patient's fingernail and the detector is located opposite the emitter on the patient's finger pad. During operation, the emitter shines one or more wavelengths of light through the patient's fingertip, or other tissue, and the light received by the detector is processed to determine various physiological characteristics of the patient.

Reflectance type sensors generally operate under the same general principles as transmittance type sensors. However, reflectance type sensors include an emitter and detector that are typically placed on the same side of the sensor site. For example, a reflectance type sensor may be placed on a patient's fingertip such that the emitter and detector are positioned side-by-side. Reflectance type sensors detect light photons that are scattered back to the detector.

For pulse oximetry applications using either transmission or reflectance type sensors the oxygen saturation of the patient's arterial blood may be determined using two or more wavelengths of light, most commonly red and near infrared wavelengths. Similarly, in other applications a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of infrared, visible, ultraviolet, or even X-ray electromagnetic radiation, and may also include any wavelength within the infrared, visible, ultraviolet, or X-ray spectra.

Pulse oximetry and other spectrophotometric sensors, whether transmission-type or reflectance-type, are typically placed on a patient in a location conducive to measurement of the desired physiological parameters. For example, pulse oximetry sensors are typically placed on a patient in a location that is normally perfused with arterial blood to facilitate measurement of the desired blood characteristics, such as arterial oxygen saturation measurement ($SaO_2$). Common pulse oximetry sensor sites include a patient's fingertips, toes, forehead, or earlobes. Regardless of the placement of the bi-stable sensor 10, the reliability of the pulse oximetry measurement is related to the accurate detection of transmitted light that has passed through the perfused tissue and has not been inappropriately supplemented by outside light sources or modulated by subdermal anatomic structures. Such inappropriate supplementation and/or modulation of the light transmitted by the sensor can cause variability in the resulting pulse oximetry measurements.

As noted above, the bi-stable sensor 10 discussed herein may be configured for either transmission or reflectance type sensing. For simplicity, the exemplary embodiment of the bi-stable sensor 10 described herein is adapted for use as a transmission-type sensor. As will be appreciated by those of ordinary skill in the art, however, such discussion is merely exemplary and is not intended to limit the scope of the present technique.

Referring now to FIGS. 2-5, an internal frame 30 for a bi-stable sensor 10 is depicted. In the depicted example, the internal frame 30 is a skeletal frame for a bi-stable sensor 10. Such a skeletal frame may include different structures or regions that may or may not have similar rigidities. For example, the depicted skeletal frame includes structural supports 34 that define the general shape of the sensor 10 when coated, as discussed below with regard to FIGS. 6-10. In view of their structure providing function, the structural supports 34 may be constructed to be substantially rigid or semi-rigid. In addition, the skeletal frame may include a cable guide 36 through which a cable, such as an electrical or optical cable, may pass to connect to the electrical or optical conductors attached to the emitter 22 and/or detector 24 upon assembly. Likewise, a skeletal frame, such as the depicted internal frame 30, may include component housings, such as the emitter housing 38 and detector housing 40 and struts 42 attaching such housings to the remainder of the skeletal frame. The struts 42 may be relatively flexible, allowing the emitter housing 38 and/or the detector housing 40 to move vertically (such as along an optical axis between the respective housings) relative to the structural supports 34 of the skeletal frame. Alternatively, in embodiments where the struts 42 are relatively rigid, where multiple struts 42 are employed to attach the housings 38 and 40 to the structural supports 34, or where the internal frame is substantially solid instead of skeletal, the housings 38 and/or 40 may be fixed relative to the respective structural supports 34 and, therefore, move with the structural supports 34.

Figure 2:
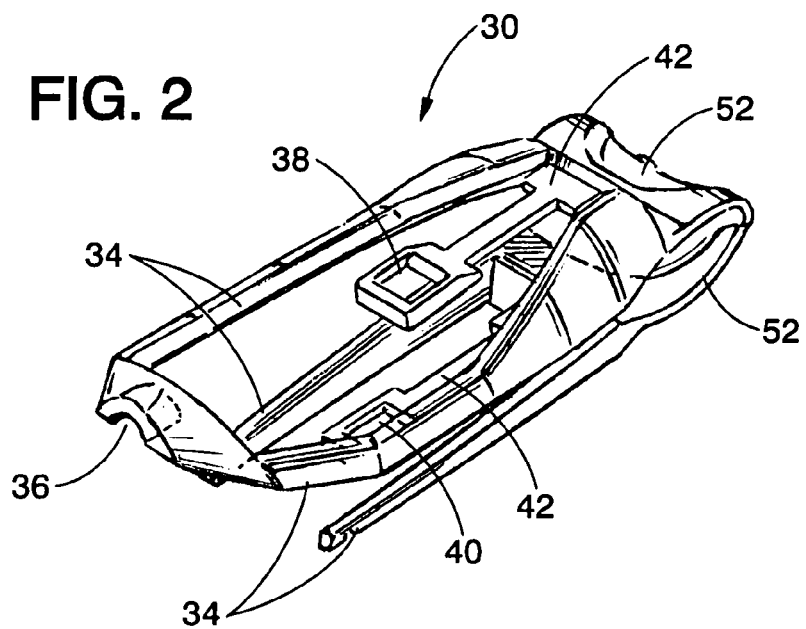
FIG. 2 illustrates a closed internal frame for use in a bi-stable sensor, in accordance with aspects of the present technique.

In embodiments where the internal frame 30 is skeletal, the various structural supports 34, housings 38 and 40, struts 42, and other structures may define various openings and spaces between and/or around the structures of the skeletal frame. In this manner, the skeletal frame provides structural support at specific locations for a coating or overmolding. However, in regions where structural support is not provided, flexibility and freedom of motion in an overlying coating or overmolding may be possible. For example, in one implementation, the emitter housing 38 and/or the detector housing 40 may be attached to the remainder of the skeletal frame by flexible struts 42, as depicted in FIG. 2. In such implementations, a coating provided proximate to the emitter housing 38 and/or detector housing 40 may be sufficiently flexible (such as due to the elasticity and/or the thinness of the coating material in the open areas of the skeletal frame) such that the housings 38 and 40 may move independent of the structural supports 34 of the frame 30 along an optical axis between the housings 38 and 40.

In certain embodiments, the internal frame 30 is constructed, in whole or in part, from polymeric materials, such as thermoplastics, capable of providing a suitable rigidity or semi-rigidity for the different portions of the internal frame 30. Examples of such suitable materials include polyurethane, polypropylene and nylon, though other polymeric materials may also be suitable. In other embodiments, the internal frame 30 is constructed, in whole or in part, from other suitably rigid or semi-rigid materials, such as stainless steel, aluminum, magnesium, graphite, fiberglass, or other metals, alloys, or compositions that are sufficiently ductile and/or strong. For example, metals, alloys, or compositions that are suitable for diecasting, sintering, lost wax casting, stamping and forming, and other metal or composition fabrication processes may be used to construct the internal frame 30.

In addition, the internal frame 30 may be constructed as an integral structure or as a composite structure. For example, in one embodiment, the internal frame 30 may be constructed as a single piece from a single material or from different materials. Alternatively, the internal frame 30 may be constructed or assembled from two or more parts that are separately formed. In such embodiments, the different parts may be formed from the same or different materials. For example, in implementations where different parts are formed from different materials, each part may be constructed from a material having suitable mechanical and/or chemical properties for that part. The different parts may then be joined or fitted together to form the internal frame 30.

Figure 3:
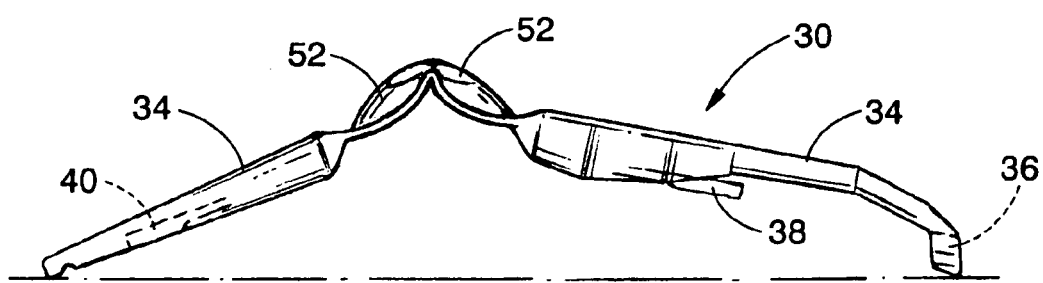
FIG. 3 illustrates a side view of the internal frame of FIG. 2 in an open configuration.

In addition, the internal frame 30 may be molded, formed, or constructed in a different configuration than the final sensor configuration. For example, the internal frame 30 for use in the bi-stable sensor 10 may be initially formed in a generally open, or flat, configuration, as depicted in FIG. 3. The internal frame 30 may then be bent from the open configuration into a relatively closed configuration, as depicted in FIG. 4.

In certain embodiments, the internal frame 30 is fitted with a resistance component, such as an elastic band 50 fitted about a hinge region 52, as depicted in FIGS. 5A and 5B. The resistance component provides or augments a resistance to transitions between configurations of the bi-stable sensor 10, as depicted generally by arrows generally indicative of the direction force (F) is applied by the resistance component. That is, the resistance provided or augmented by the resistance component is overcome to transition between two mechanically stable sensor configurations. For example, in FIG. 5A, the resistance component provides force, F, that biases a first portion 54 and a second portion 56 of the internal frame 30 closed absent a greater opposing force, i.e., an opening force. Likewise, in FIG. 5B, the resistance component provides force, F, that biases the first portion 54 and second portion 56 of the internal frame 30 apart absent a greater opposing force, i.e., a closing force.

As will be appreciated by those of ordinary skill in the art, a resistance component, such as elastic band 50, may be composed of a material or a combination of materials that provide the desired elasticity and resistance, such as polymeric materials (rubber, plastic, and so forth) or metals. Likewise, the resistance component may take other forms than a continuous loop, such as the exemplary elastic band 50. For example, an elastic band or strap may be configured with dove-tailed ends or with a dog-bone shape to facilitate connection to the frame 30, such as to conform to complementary attachment regions integral to the frame 30.

Though the present example depicts the resistance component, in the form of elastic band 50, as being disposed directly on the frame 30, one of ordinary skill in the art will appreciate that other configurations are also possible. For example, the resistance component, such as elastic band 50, may be disposed within a coating material overlying the frame 30 or external to such a coating material. Similarly, in other embodiments, the resistance component may be provided as part of the frame 30, such as a hinge portion 52 configured to resist transitions between stable configurations (without augmentation by an added resistance component). Likewise, the resistance component may be or may include an elastomeric coating material, as discussed below, disposed over the frame 30. In such embodiments, the coating material may provide the resistance based on the elasticity or other physical properties of the coating material itself. Alternatively, the resistance provided by the coating may be based on regions of the coating that differ in elasticity and/or hardness, thereby forming resistive structures or regions within the coating.

As noted above, in certain embodiments of the present technique, the frame 30 (such as a skeletal, internal frame) is coated to form a unitary or integral sensor assembly, as depicted in FIGS. 6-10. Such overmolded embodiments may result in a sensor assembly in which the internal frame 30 is completely or substantially coated. In embodiments in which the internal frame 30 is formed or molded as a relatively open or flat structure, the overmolding or coating process may be performed prior to or subsequent to bending the internal frame 30 into the closed configuration.

For example, the bi-stable sensor 10 may be formed by an injection molding process. In one example of such a process the internal frame 30, with or without an attached elastic band 50, may be positioned within a die or mold of the desired shape for the bi-stable sensor 10. A molten or otherwise unset overmold material may then be injected into the die or mold. For example, in one implementation, a molten thermoplastic elastomer at between about 400° F. to about 450° F. is injected into the mold. The overmold material may then be set, such as by cooling for one or more minutes or by chemical treatment, to form the sensor body about the internal frame 30 and the elastic band 50, if present. In certain embodiments, other sensor components, such as the emitter 22 and/or detector 24, may be attached or inserted into their respective housings or positions on the overmolded sensor body.

Alternatively, the optical components (such as emitter 22 and detector 24) and/or conductive structures (such as wires or flex circuits) may be placed on the internal frame 30 prior to overmolding. The internal frame 30 and associated components may then be positioned within a die or mold and overmolded, as previously described. To protect the emitter 22, detector 24, and or other electrical components, conventional techniques for protecting such components from excessive temperatures may be employed. For example, the emitter 22 and/or the detector 24 may include an associated clear window, such as a plastic or crystal window, in contact with the mold to prevent coating from being applied over the window. In one embodiment, the material in contact with such windows may be composed of a material, such as beryllium copper, which prevents the heat of the injection molding process from being conveyed through the window to the optical components. For example, in one embodiment, a beryllium copper material initially at about 40° F. is contacted with the windows associated with the emitter 22 and/or detector 24 to prevent coating of the windows and heat transfer to the respective optical components. As will be appreciated by those of ordinary skill in the art, the injection molding process described herein is merely one technique by which the frame 30 may be coated to form a sensor body, with or without associated sensing components. Other techniques which may be employed include, but are not limited to, dipping the frame 30 into a molten or otherwise unset coating material to coat the frame 30 or spraying the frame 30 with a molten or otherwise unset coating material to coat the frame 30. In such implementations, the coating material may be subsequently set, such as by cooling or chemical means, to form the coating. Such alternative techniques, to the extent that they may involve high temperatures, may include thermally protecting whatever optical components are present, such as by using beryllium copper or other suitable materials to prevent heat transfer through the windows associated with the optical components, as discussed above.

By such techniques, the frame 30, as well as the optical components and associated circuitry where desired, may be encased in a coating material 60 to form an integral or unitary assembly with no exposed or external moving parts of the frame 30. For example, as depicted in FIGS. 6 and 7, the bi-stable sensor 10 includes features of the underlying internal frame 30 that are now completely or partially overmolded, such as the overmolded emitter housing 62 and detector housing 64. In addition, the overmolded bi-stable sensor 10 includes an overmolded upper portion 70 and lower portion 72 that may be fitted to the finger, toe, ear, or other appendage of a patient when the bi-stable sensor 10 is in a closed configuration.

In one implementation, the overmolding or coating 60 is a thermoplastic elastomer or other conformable coating or material. In such embodiments, the thermoplastic elastomer may include compositions such as thermoplastic polyolefins, thermoplastic vulcanizate alloys, silicone, thermoplastic polyurethane, and so forth. As will be appreciated by those of ordinary skill in the art, the overmolding composition may vary, depending on the varying degrees of conformability, durability, wettability, elasticity, or other physical and/or chemical traits that are desired.

Figure 8:
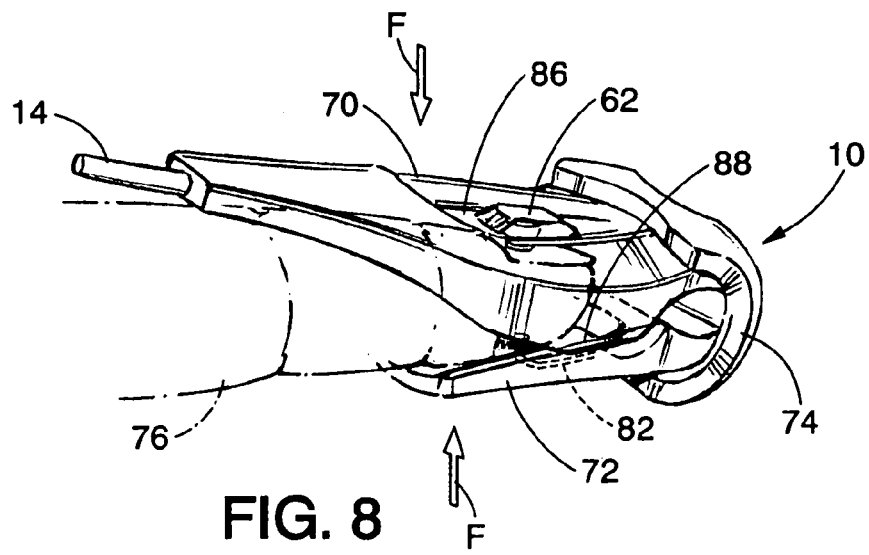
FIG. 8 illustrates the bi-stable sensor of FIG. 6 in use on a patient's finger, in accordance with aspects of the present technique.

Furthermore, the coating material 60 may be selected or configured to provide some or all of the resistance to transitions of the bi-stable sensor 10 between open and closed configurations, as depicted in FIGS. 6 and 7. For example, referring now to FIGS. 6 and 7, the coating material 60 may be disposed as a thick region 74 or layer about the hinge region of the bi-stable sensor (generally corresponding to the overmolded hinge region 52 of the frame 30). In this manner, the thickness of the thick region 74 and the elasticity of the coating material 60 may provide resistance, indicated by force arrows, F, which opposes transitions between different configurations of the bi-stable sensor 10. For example, as depicted in FIG. 7, in an open configuration, the resistance provided by the thick region 74 of coating material acts to bias the upper portion 70 and lower portion 72 of the sensor body 10 apart. A sufficient opposing or closing force, however, may overcome the resistance provided by the thick region 74 of coating material, to transition the sensor body 10 a closed configuration, as depicted in FIG. 6. Once in the closed configuration, the thick region 74 of coating material then resists transition to the open configuration, as indicated by force arrows, F, in FIG. 6. As will be appreciated by those of ordinary skill in the art, in the closed configuration, the upper portion 70 and lower portion 72 may be partially separated without fully overcoming the resistance to transition, i.e., without "opening" the sensor 10, allowing the sensor 10 to be comfortably and conformably fitted to a patient's finger 76, as depicted in FIG. 8, or to a patient's toe, ear, and so forth, in other embodiments.

The depicted sensor 10, therefore, has two mechanically stable configurations, i.e., it is bi-stable, with each stable configuration resisting change absent a force sufficient to overcome the resistance provided by the sensor itself. As will be appreciated by those of ordinary skill in the art, the resistance to transitioning between stable configurations may depend on various factors, such as those described by example herein. For example, to the extent that the resistance is provided at least partly by a thick region 74 of coating material, as depicted in FIGS. 6 and 7, the resistance may be a function of the thickness of the thick region 74, the elasticity and/or hardness of the coating material 60, and the presence of additional resistive structure within or about the thick region 74. For instance, the thick region 74 may be composed of coating material 60 having uniform composition, elasticity, hardness, and so forth. Alternatively, the thick region 74 may be composed of more than one type of coating material 60, with the different coating materials having different elasticities, hardnesses, or other mechanical properties that affect the resistance to transition between stable configurations of the sensor 10. Furthermore, the thick region 74 of coating material may overlie, incorporate, or support an additional resistive structure, such as an elastic band 50 disposed about the hinge region 52 of the frame. Therefore, as will be appreciated by those of ordinary skill in the art, the resistance opposing transitions between stable configurations of the sensor 10 may be determined by a variety of factors, such as the thickness of the coating material 60 about a hinge of the sensor 10, the composition, configuration, and/or uniformity of the coating material 60 about the hinge of the sensor 10, the construction or inclusion of additional resistive structures about the hinge of the sensor 10, as well as other possible factors.

While selection of the coating material 60 may be based upon the resistance considerations noted above, the coating material 60 may also be selected based upon the desirability of a chemical bond between the internal frame 30 and the coating material 60. Such a chemical bond may be desirable for durability of the resulting overmolded bi-stable sensor 10. For example, to prevent separation of the coating 60 from the internal frame 30, the material used to form the coating 60 may be selected such that the coating 60 bonds with some or all of the internal frame 30 during the overmolding process. In such embodiments, the coating 60 and the portions of the internal frame 30 to which the coating 60 is bonded are not separable, i.e., they form one continuous and generally inseparable structure.

Furthermore, in embodiments in which the coating 60 employed is liquid or fluid tight, such a bi-stable sensor 10 may be easily maintained, cleaned, and/or disinfected by immersing the sensor into a disinfectant or cleaning solution or by rinsing the sensor 10 off, such as under running water. For example, in an open configuration of the sensor 10, as depicted in FIG. 7, and the sensor 10 may be immersed or rinsed with water or a disinfectant solution for easy cleaning. Of course, the bi-stable sensor 10 may be cleaned in either the closed or open configuration. In particular, the overmolded bi-stable sensor 10 may be generally or substantially free of crevices, gaps, junctions or other surface irregularities typically associated with a multi-part construction which may normally allow the accumulation of biological detritus or residue. Such an absence of crevices and other irregularities may further facilitate the cleaning and care of the sensor 10.

Figure 9:
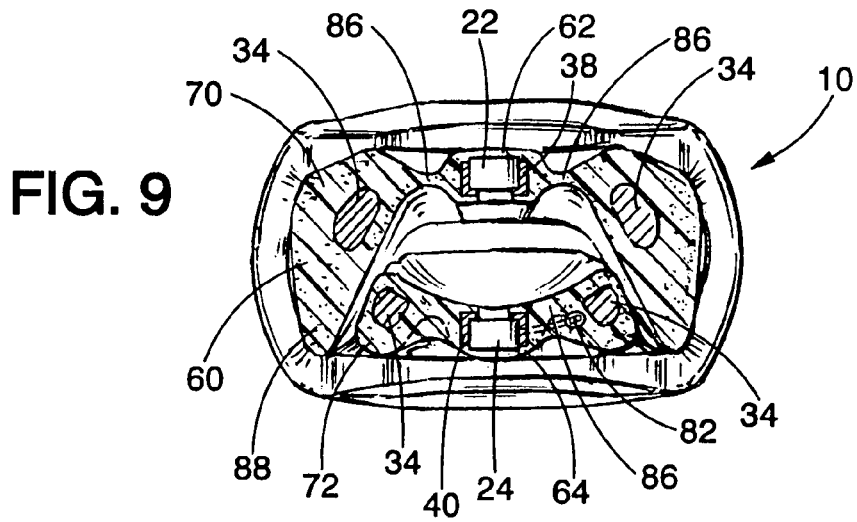
FIG. 9 illustrates a cross-section taken along section line 9 of FIG. 6.
Figure 10:
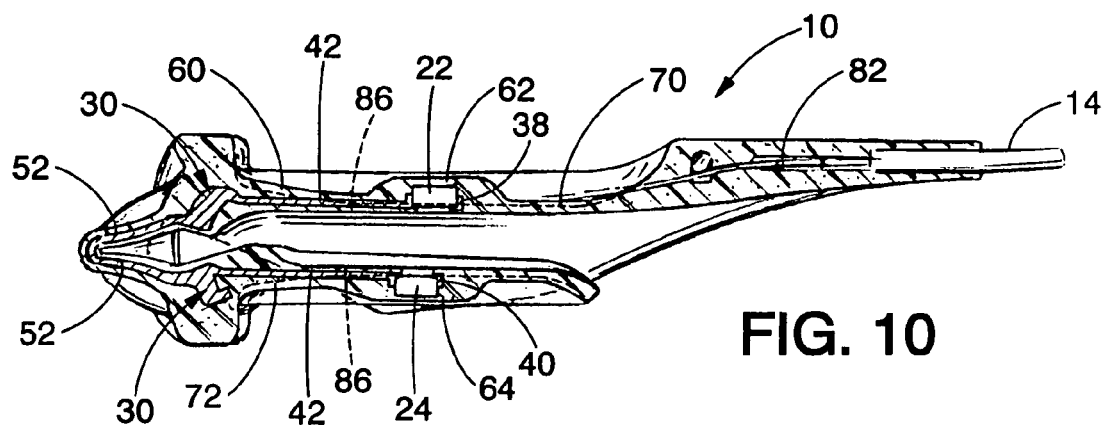
FIG. 10 illustrates a cross-section taken along section line 10 of FIG. 6.

Turning now to FIGS. 9 and 10, cross-sections of the coated bi-stable sensor 10 in a closed configuration are depicted taken through transverse optical planes, represented by section line 8 and 9 of FIG. 6 respectively. FIGS. 8 and 9 depict, among other aspects of the bi-stable sensor 10, the overmolding material 60 as well as underlying portions of the internal frame 30, such as the emitter housing 38 and detector housing 40, along with the respective emitter 22, detector 24, and signal transmission structures (such as wiring 82 or other structures for conducting electrical or optical signals). In the depicted embodiment, the emitter 22 and detector 24 are provided substantially flush with the patient facing surfaces of the bi-stable sensor 10, as may be suitable for pulse oximetry applications. For other physiological monitoring applications, such as applications measuring tissue water fraction or other body fluid related metrics, other configurations may be desirable. For example, in such fluid measurement applications it may be desirable to provide one or both of the emitter 22 and detector 24 recessed relative to the patient facing surfaces of the bi-stable sensor 10. Such modifications may be accomplished by proper configuration or design of a mold or die used in overmolding the internal frame 30 and/or by proper design of the emitter housing 38 or detector housing 40 of the internal frame 30.

In addition, as depicted in FIGS. 9 and 10, in certain embodiments portions 86 of the coating material 60 may be flexible, such as thin or membranous regions of coating material 60 disposed between structural supports 34 of a skeletal frame. Such flexible regions 86 allow a greater range of digit sizes to be accommodated for a given retention or clamping force of the sensor 10. For example, the flexible regions 86 may allow the emitter 22 and/or detector 24, to flex or expand apart from one another along the optical axis in embodiments in which the respective housings 38 and 40 are flexibly attached to the remainder of the frame 30. In this manner, the sensor 10 may accommodate differently sized digits. For instance, for a relatively small digit, the flexible regions 86 may not be substantially deformed or vertically displaced, and therefore the emitter 22 and/or detector 24 are not substantially displaced either. For larger digits, however, the flexible regions 86 may be deformed or displaced to a greater extent to accommodate the digit, thereby displacing the emitter 22 and/or detector 24 as well. In addition, for medium to large digits, the flexible regions 86 may also increase retention of the sensor 10 on the digit by increasing the surface area to which the retaining force is applied.

Furthermore, as the flexible regions 86 deform, the force applied to the digit is spread out over a large area on the digit due to the deformation of the flexible region 86. In this way, a lower pressure on digits of all sizes may be provided for a given vertical force. Therefore, a suitable conforming fit may be obtained in which the emitter 22 and detector 24 are maintained in contact with the digit without the application of concentrated and/or undesirable amounts of force, thereby improving blood flow through the digit.

In the example depicted in FIGS. 6-10, flaps or side extensions 88 of the coating material 60 on the sides of the bi-stable sensor 10 are depicted which facilitate the exclusion of environmental or ambient light from the interior of the bi-stable sensor 10. Such extensions help prevent or reduce the detection of light from the outside environment, which may be inappropriately detected by the sensor 10 as correlating to the $SaO_2$. Thus, the pulse oximetry sensor may detect differences in signal modulations unrelated to the underlying $SaO_2$ level. In turn, this may impact the detected red-to-infrared modulation ratio and, consequently, the measured blood oxygen saturation ($SpO_2$) value. The conformability of the fit of sensor 10 and the use of side extensions 88, therefore, may help prevent or reduce such errors.

While the exemplary bi-stable sensors 10 discussed herein are some examples of overmolded or coated medical devices, other such devices are also contemplated and fall within the scope of the present disclosure. For example, other medical sensors and/or contacts applied externally to a patient may be advantageously applied using a bi-stable sensor body as discussed herein. Examples of such sensors or contacts may include glucose monitors or other sensors or contacts that are generally held adjacent to the skin of a patient such that a conformable and comfortable fit is desired. Similarly, and as noted above, devices for measuring tissue water fraction or other body fluid related metrics may utilize a sensor as described herein. Likewise, other spectrophotometric applications where a probe is attached to a patient may utilize a sensor as described herein.

In addition, overmolded bi-stable medical devices for use invasively, i.e., within the patient, are also presently contemplated. For example, clamps or other medical devices used invasively may be designed as bi-stable devices, i.e., having an open and a closed position, in which the transition between configurations is accomplished using a substantial force, thereby preventing incidental or accidental transitions between open and closed configurations. Furthermore, an overmolding or other coating may be provided on such devices, such as where non-reactivity with bodily fluids or tissues is desired, or where it is generally desired to provide an invasive device having few or no exposed niches or crevices or where it is generally desired to coat the internal framework or skeleton of a device.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, the present techniques may not only be applied to transmission type sensors for use in pulse oximetry, but also to retroflective and other sensor designs as well. Likewise, the present techniques are not limited to use on fingers and toes but may also be applied to placement on other body parts such as in embodiments configured for use on the ears or nose.

What is claimed is:

1. A sensor assembly, comprising:
   a frame comprising a first portion and a second portion connected by a hinge;
   an emitter disposed on the frame;
   a detector disposed on the frame;
   a coating molded over the frame, the emitter, and the detector to form a unitary sensor assembly; and
   a resistance-providing component disposed generally about the hinge.

2. The sensor assembly of claim 1, wherein the resistance-providing component comprises one or more elastic bands disposed beneath the coating.

3. The sensor assembly of claim 1, wherein the resistance-providing component comprises one or more elastic bands disposed external to the coating.

4. The sensor assembly of claim 1, wherein the resistance-providing component comprises one or more elastic bands disposed within the coating.

5. The sensor assembly of claim 1, wherein the resistance-providing component comprises a region of the coating.

6. The sensor assembly of claim 1, wherein the resistance-providing component comprises a thick region of the coating.

7. The sensor assembly of claim 1, comprising one or more signal transmission structures connected to at least one of the emitter or the detector.

8. The sensor assembly of claim 1, wherein the unitary sensor assembly comprises at least one of a pulse oximetry sensor, a sensor for measuring a water fraction, or a combination thereof.

9. The sensor assembly of claim 1, wherein the frame comprises a single molded part.

10. The sensor assembly of claim 1, wherein the frame comprises two or more parts joined to form the frame.

11. The sensor assembly of claim 1, wherein the resistance-providing component comprises at least one of a polymeric material or a metal.

12. The sensor assembly of claim 1, wherein the coating comprises a thermoplastic elastomer.

13. The sensor assembly of claim 12, wherein the thermoplastic elastomer comprises at least one of a thermoplastic polyolefin, a thermoplastic vulcanizate alloy, thermoplastic polyurethane, silicone, or a combination thereof.

14. The sensor assembly of claim 1, wherein the coating comprises a conformable material.

15. The sensor assembly of claim 1, wherein no moving parts of the frame remain exposed from the coating.

16. The sensor assembly of claim 1, wherein the unitary sensor assembly is configured to move between at least two mechanically stable configurations.

17. The sensor assembly of claim 16, wherein the unitary sensor assembly is configured to move between the at least two mechanically stable configurations when a resistance provided at least partially by the resistance-providing component is overcome.

18. The sensor assembly of claim 1, wherein the sensor assembly is fluid tight.

19. The sensor assembly of claim 1, wherein the coating is chemically bonded to the frame.

20. The sensor assembly of claim 1, comprising a pulse oximeter monitor configured to receive data from the unitary sensor assembly.

21. The sensor assembly of claim 1, comprising a multi-parameter monitor configured to receive data from the unitary sensor assembly.

22. The sensor assembly of claim 1, comprising at least one integrated circuit device.

23. The sensor assembly of claim 1, comprising a cable comprising one or more integrated circuits.

24. The sensor assembly of claim 1, comprising an adapter cable connected to one or more signal transmission structures of the unitary sensor assembly.

25. The sensor assembly of claim 1, wherein the coating comprises one or more regions configured to allow at least one of the emitter or the detector to be displaced relative to a substantially rigid portion of the frame upon placement of the unitary sensor assembly on a patient.

26. The sensor assembly of claim 1, wherein the resistance-providing component biases the unitary sensor assembly open in a first configuration and biases the unitary sensor assembly closed in a second configuration.

27. The sensor assembly of claim 1, wherein the emitter comprises one or more light emitting diodes.

28. The sensor assembly of claim 1, wherein the detector comprises a photodetector.

* * * * *

UNITED STATES PATENT AND TRADEMARK OFFICE
CERTIFICATE OF CORRECTION

PATENT NO. : 7,657,296 B2 Page 1 of 1
APPLICATION NO. : 11/495392
DATED : February 2, 2010
INVENTOR(S) : Raridan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 552 days.

Signed and Sealed this

Thirtieth Day of November, 2010

David J. Kappos
*Director of the United States Patent and Trademark Office*